United States Patent [19]
Malcom et al.

[11] Patent Number: 4,583,555
[45] Date of Patent: Apr. 22, 1986

[54] KNEE LIGAMENT TESTING SYSTEM

[75] Inventors: Lawrence L. Malcom, San Diego; Dale M. Daniel, La Mesa; Conny M. Jamison, San Diego; Robert E. Landesman, Encinitas, all of Calif.

[73] Assignee: Medmetric Corporation, San Diego, Calif.

[21] Appl. No.: 455,248

[22] Filed: Jan. 3, 1983

[51] Int. Cl.[4] ............................................... A61B 5/10
[52] U.S. Cl. ..................................................... 128/782
[58] Field of Search ...................... 128/774, 782, 92 E; 33/174 D

[56] References Cited

U.S. PATENT DOCUMENTS

| | | | |
|---|---|---|---|
| 1,662,670 | 9/1927 | Harter | 33/174 D |
| 1,944,601 | 1/1934 | Gulick | 33/174 D |
| 1,976,045 | 10/1934 | Sorenson | 33/174 D |
| 2,107,534 | 2/1938 | Houser | 33/174 D |
| 4,470,810 | 9/1984 | Bourdeau et al. | 33/174 D |

OTHER PUBLICATIONS

Torg et al., Amer. J. of Sports Med., vol. 4, No. 2, Mar./Apr. 1976, pp. 84–93.
Markolf et al., J. of Bone and Joint Surgery, vol. 60-A, No. 5, Jul. 1978, pp. 664–674.
Kennedy et al., J. of Bone and Joint Surgery, vol. 53-A, 1971, pp. 1257–1270.
Crowninshield et al., J. of Biomechanics, vol. 9, 1976, pp. 529–535.

*Primary Examiner*—Kyle L. Howell
*Assistant Examiner*—John C. Hanley
*Attorney, Agent, or Firm*—Albert L. Gabriel

[57] ABSTRACT

A tibia-referenced system for objectively testing the integrity of the anterior and posterior cruciate ligaments of the knee with passive drawer, active drawer, and end point tests. Two simplified forms of the invention embody an elongated reference arm with a distal end pad that is fulcrumed against a distal region on the tibia and a proximal reference pad that rests on either the tibial tubricle or patellar bone structure, while a displacement indicator rod slidably mounted on the arm carries another proximal reference pad that rests on the other of these two bone structures adjacent the knee joint. In a third form of intermediate complexity, the second reference structure, instead of the indicator rod, is a second elongated reference arm distally pivotally connected to the other reference arm, each of the two arms carrying a reference pad that rests on a respective one of the tibial tubricle and pateller bone structures; and in this form the relative angular pivotal positions of the arms is translated to a displacement indicator dial that provides a direct readout of anterior or posterior drawer shift. The fourth and most complex form of the invention has the distally pivoted reference arms and direct readout displacement indicator dial of the third form, and further includes a case in which the arms are pivoted that is strapped against the tibia, with a force-applying handle extending anteriorly of the case and a force-indicating transducer operatively arranged between the handle and the case to audibly indicate predetermined applied force levels.

18 Claims, 25 Drawing Figures

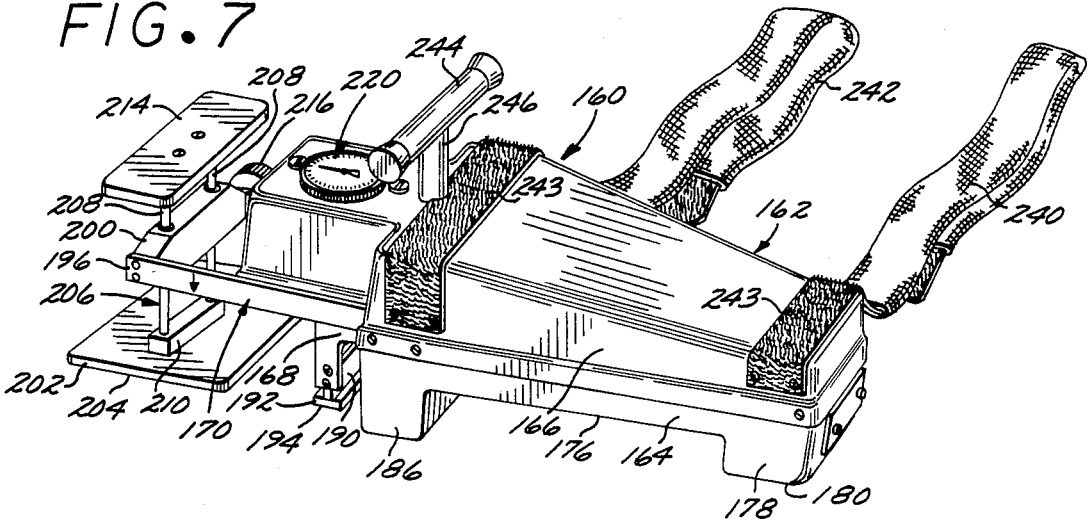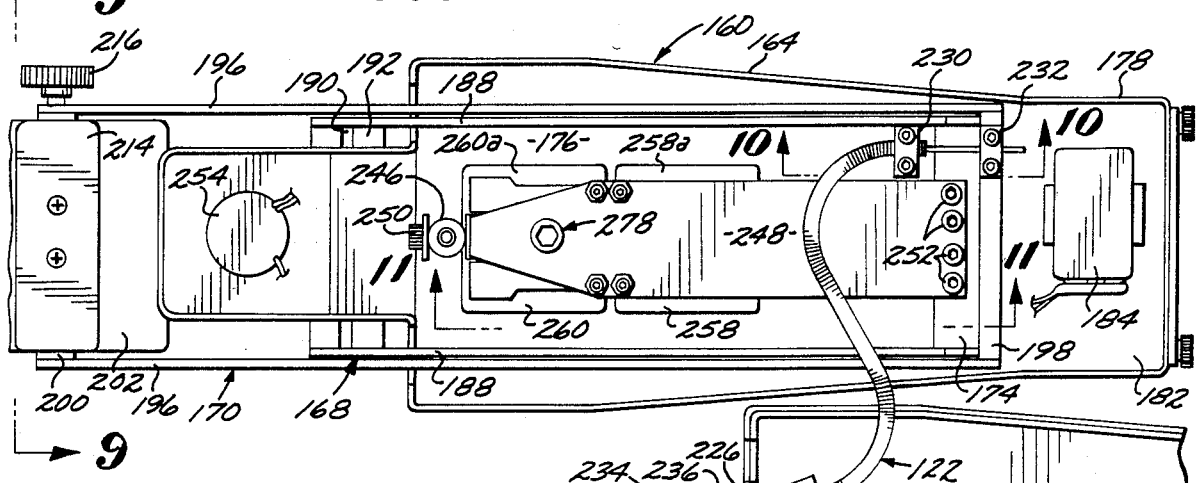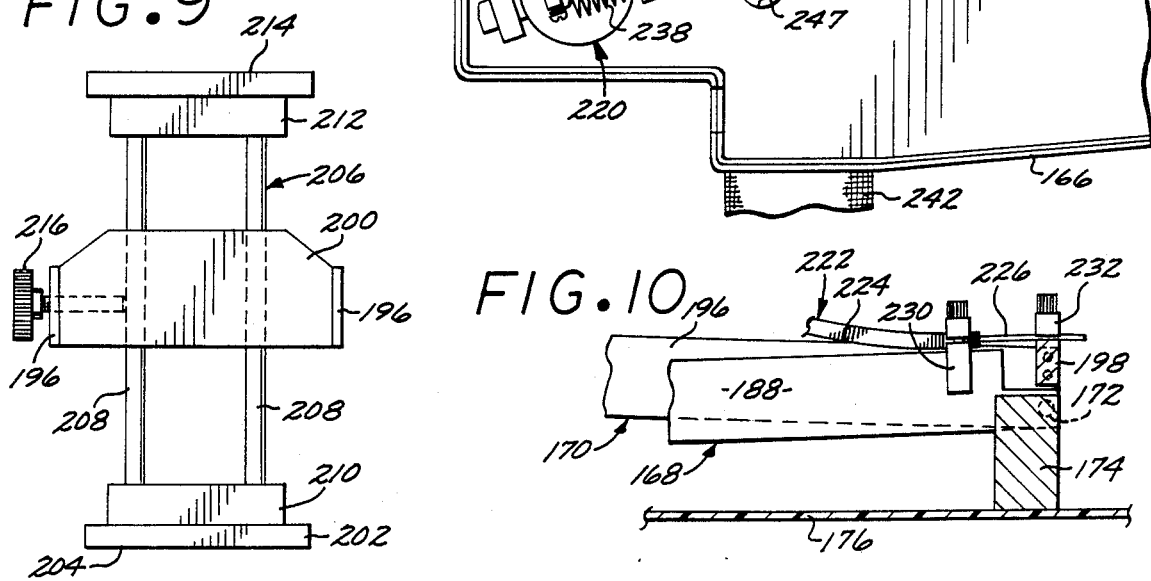

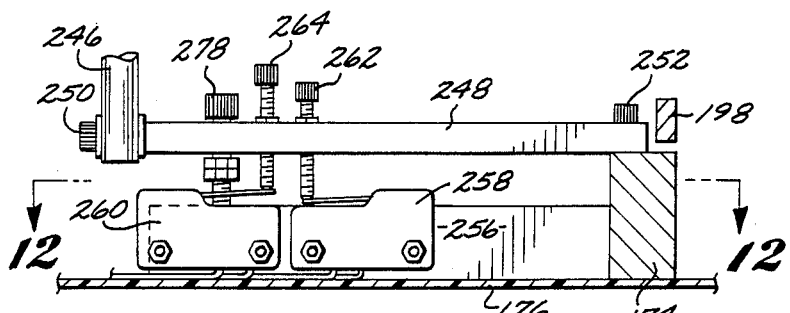
FIG.11
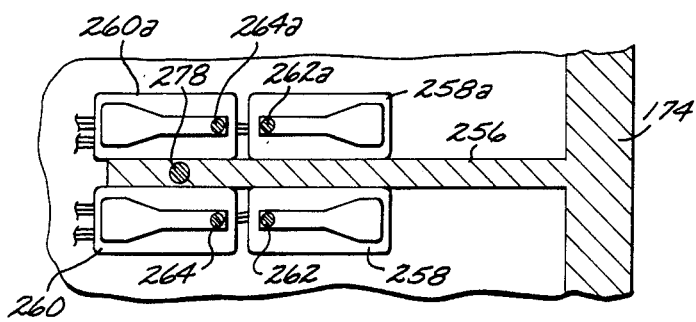
FIG.12
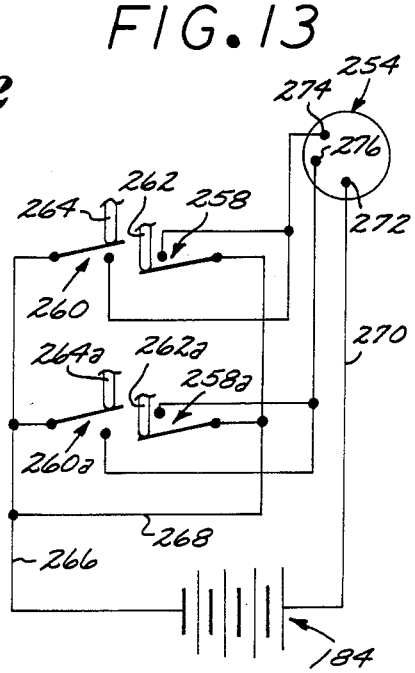
FIG.13
FIG.15
FIG.14
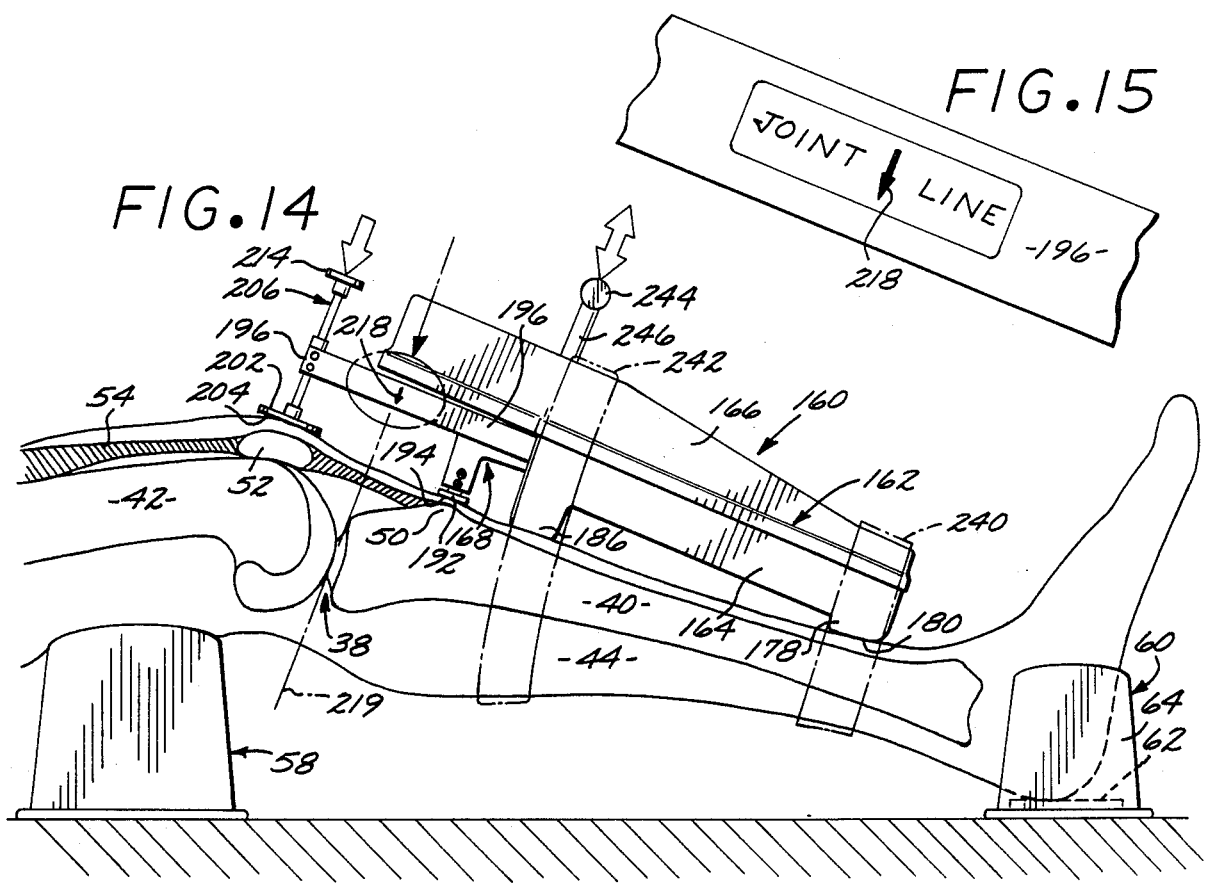

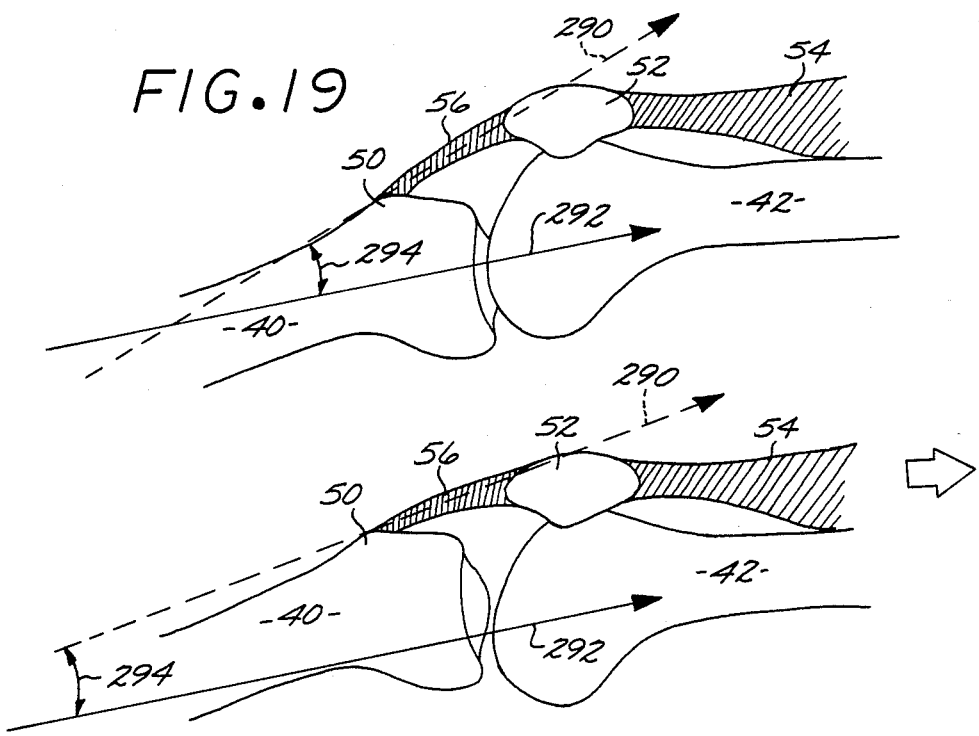
FIG.19
FIG.20
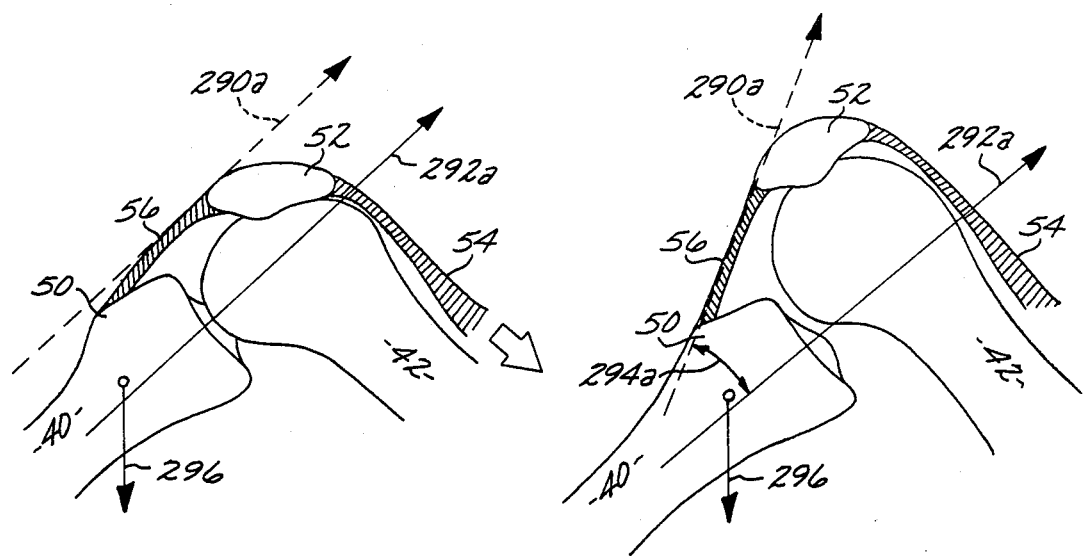
FIG.21
FIG.22

KNEE LIGAMENT TESTING SYSTEM

BACKGROUND OF THE INVENTION

1. One Field of the Invention

The present invention is in the field of knee ligament testing systems, and it relates particularly to apparatus and methods for measuring anterior and posterior drawer shift or displacement of the proximal tibia relative to the distal femur as a result of applied forces so as to determine the presence or absence of a torn anterior or posterior cruciate ligament, respectively.

2. Description of the Prior Art

The clinical test which is the most similar to the method of the present invention for determining a disrupted or torn anterior cruciate ligament is known as the "Lachman" test. The Lachman test has been taught for many years by John W. Lachman, Chairman and Professor of Orthopedic Surgery at Temple University. The Lachman test is described in considerable detail by Torg, J. S., Conrad, W., and Kalen, V. in an article entitled "Clinical Diagnosis of Anterior Cruciate Ligament Instability in the Athlete", in The American Journal of Sports Medicine, Vol. 4, No. 2, March/April, 1976 at pages 84–93. In performing the Lachman test, the patient lies supine on a table with the knee held between full extension and 15° of flexion. The person performing the test holds the thigh in one hand and the calf in the other, applying a firm anterior pressure to the calf in an attempt to translate the proximal tibia anteriorly relative to the distal femur. A positive test which indicates a torn or disrupted anterior cruciate ligament is one in which there is proprioceptive and/or visual anterior translation of the tibia in relation to the femur with a characteristic "mushy" or "soft" end point. This is in contrast to a definite "hard" end point elicited when the anterior cruciate ligament is intact.

The principal failing of the Lachman test is that it is entirely subjective and provides no measurement of knee displacement. Thus, the Lachman test provides no objective basis for comparison either with the sound knee of the patient or with statistical information relating the amount of displacement to the condition of the anterior cruciate ligament. The entirely subjective nature of the Lachman test also precludes its use in the development of any statistical information comparing anterior drawer shifts between uninjured and injured knees.

Another problem with the Lachman test is that the required grasping of the thigh and calf in the hands of the tester tends to cause patient guarding or resistance by muscular contraction, which will mask the true condition of the anterior cruciate ligament. The Lachman test is useless in the case of an acute knee injury (within seven days of the occurrence of the injury) when the knee joint is usually still swollen and painful, which greatly increases patient guarding. Further problems with the Lachman test are that a person with small hands has difficulty performing this test; and even with large hands the thigh and calf of an obese person cannot be adequately grasped to perform the test.

The first system capable of measuring or documenting the anterior or posterior displacement of the proximal tibia relative to the distal femur was that of J. C. Kennedy and P. J. Fowler, who described their system in an article entitled "Medial and Anterior Instability of the Knee. An Anatomical and Clinical Study Using Stress Machines," Journal of Bone and Joint Surgery, Vol. 53-A, 1971, at pages 1257-1270. According to the Kennedy and Fowler system, the patient was strapped upright into an immovable seat resembling a hydraulic barber's chair and the foot strapped down with the knee bent to 90° of flexion. An anterior pulling force or a posterior pushing force was applied to the proximal tibia by gas-pressurized actuator cylinders. X-Rays were taken of the tibia and femur relative positions before and after the force was applied, and the displacements were recorded by directly measuring the motions seen on the X-Ray films. This system had the disadvantage that it had no direct mechanical means for indicating or measuring the tibial displacements relative to the femur as they occurred, as well as the inherent disadvantages of X-Rays. Another, major disadvantage of this system was that it attempted to immobilize the femur in what can be considered to be an earth-based or chair-based system. The problem with such reliance upon the supposed immobilization of the femur is that the femur is encased in a large amount of muscle tissue which, when relaxed as required for such testing, provides no firm locational support for the femur. On the other hand, if the muscles are tight enough for a somewhat rigid supporting of the femur, then the muscle tightness opposes the tibia/femur displacement which is the objective of the test.

A still further failing of the Kennedy and Fowler system was that their equipment was only capable of measuring knee displacements at 90° of flexion. Applicant has found that while 90° of flexion is sometimes satisfactory for posterior drawer testing, it is quite unsatisfactory for anterior drawer testing because of the large amount of posterior leverage which the powerful hamstring muscles have in opposition to the anterior drawer test, whereby only a slight amount of hamstring guarding will mask the anterior drawer test at large angles of knee flexion such as 90°. This problem is not present in the Lachman anterior drawer test, wherein the knee is between full extension and 15° of flexion.

In any earth-based or chair-based system such as that of Kennedy and Fowler, the imposing nature of the large and complex equipment, the discomfort of the apparatus employed to strap the patient down, and then the large amount of time, usually at least about 1½ hours, required to strap the patient down, adjust the equipment and take the tests, inevitably caused patient guarding that interfered with the accuracy of the tests.

Markolf, K. L., Graff-Radford, A., and Amstutz, H. C., reported the first equipment that was capable of indicating or recording anterior/posterior tibial force versus displacement. This was reported in an article entitled "In Vivo Knee Stability", in the Journal of Bone and Joint Surgery, Vol. 60-A, No. 5, July, 1978, at pages 664–674. In this system a handle attached to a force transducer is strapped around the patient's calf. The examiner manually pulls or pushes through the handle which senses the force that is being applied as a displacement transducer records the displacement of the proximal tibia relative to the patella on the femur.

The Markolf et al system is again an earth- or chair-based system which has the same failings as those pointed out hereinabove for the Kennedy and Fowler system. In the Markolf et al system the reference point for all tibial displacement measurements is the chair, so that considerable equipment is directed toward an attempt to immobilize the patient's femur. Thus, there is a system of inflatable thigh compression pads, a contoured patellar compression block, and compression of the patient's sacrum by the rigid back of the chair. Additionally, the patient's foot is strapped down. As with the Kennedy and Fowler apparatus, the Markolf et al apparatus, due to its large, complex and imposing nature, the discomfort of the strapped-down patient, and the approximately 1½ hours required to set up and perform the testing, caused considerable patient guarding that seriously interfered with the testing.

Applicant is aware of only one other type of apparatus which seeks to determine the presence or absence of a knee ligament deficit condition. This was reported by Crowninshield, R.; Pope, M. H., Johnson, R,; and Miller, R. in an article entitled "The Impedance of the Human Knee" in the Journal of Biomechanics, Vol. 9, 1976 at pages 529–535. This was laboratory apparatus which applied a cyclic rotational motion about the longitudinal axis of the tibia. By varying the frequency of the mechanical oscillation of the tibia while at the same time attempting to keep the femur relatively stable, the mechanical impedance characteristics of the knee were measured. These included the resonant frequency of oscillation of the knee, the change in the phase lag between the force input cycle and the displacement output cycle with varying frequency, and the like. Since the Crowninshield et al apparatus imposed only rotational or varus-valgus (medial and lateral bending) motions on the knee, this equipment was not capable of indicating or measuring anterior or posterior tibia/femur drawer shift to determine whether or not the anterior and posterior cruciate ligaments were torn.

A general failing in the art was the inability of any of the prior art systems to test the condition of anterior or posterior cruciate ligaments in the case of an acute knee injury, i.e., within seven days of the occurrence. This was primarily because of guarding that resulted either from hand manipulation that was required for the testing or from reaction to the discomfort of equipment used to strap down the patient's leg.

SUMMARY OF THE INVENTION

In view of these and other problems in the art, it is a general object of the present invention to provide a system for testing the condition of the anterior and posterior cruciate knee ligaments that provides an objective measurement of drawer shift or displacement between the proximal tibia and the distal femur quickly and easily, and with a minimum of discomfort to the patient.

Another object of the invention is to provide a system for testing the integrity of the anterior and posterior cruciate ligaments which, while providing an objective measurement of the tibia/femur displacement not possible with the Lachman test, nevertheless does not require that the patient be strapped down in a complicated chair arrangement attempting to immobilize the femur as in both the Kennedy et al and Markolf et al systems.

A principal object of the present invention is to provide, for the first time in this art, a tibia-referenced system for measuring anterior and posterior knee drawer shifts, as distinguished from the earth- or chair-based systems of Kennedy et al and Markolf et al; the tibia-reference system of the invention avoiding any necessity for strapping down the thigh in an attempt to immobilize the femur, and thereby enabling the thigh to rest in comfort during the testing and avoiding much of the prior art problem of patient guarding by contraction of quadriceps and/or hamstring muscles of the thigh.

A further object of the invention is to provide a knee ligament testing system which, by being a tibia-referenced system and thereby avoiding discomfort of the thigh and consequent patient guarding, for the first time enables testing for deficit conditions of the anterior and posterior cruciate ligaments in the case of an acute knee injury, i.e., within seven days of the occurrence of the injury, which can be a time of critical importance in the correction of a knee ligament deficit condition.

A further object of the invention is to provide a system for testing the integrity of the anterior and posterior cruciate ligaments of the knee which references the proximal end of the tibia and the distal end of the femur through respective accessible, generally unyielding anterior bone structures proximate the knee, namely, the tibial tubricle and the patella; this referencing through the tibial tubricle and the patella providing a much more reliable and accurate representation of the knee joint displacement than prior art earth- or chair-based systems, and avoiding the necessity for manually squeezing the area around the knee or putting the thumb on the joint line as were done in the Lachman test and which may be painful in an acutely injured patient.

A still further object of the invention is to provide a tibia-referenced knee ligament testing system with its accompanying increased accuracy and minimized patient guarding, wherein both the displacement measurement and the anterior and posterior forces applied during the testing are objective, whereby comparative test results between a patient's injured and uninjured knees or between an injured knee and statistical data representing either injured of uninjured knees, enables a reliable determination to be made as to whether or not there is a torn anterior or posterior cruciate ligament in the injured knee.

Four forms of the invention are disclosed herein, the first two being simplified forms, the third being a form of intermediate complexity but with a more directly readable tibia/femur displacement indicator, and the fourth being the most complex form disclosed and having both a direct displacement indicator and a force transducer that audibly indicates predetermined anterior- and posterior-directed force levels. Each of these four forms of the invention disclosed herein references two anterior bone structures closely adjacent to the knee joint, namely, the tibial tubricle forming a part of the tibia bone and the patella which overlies the femur bone, making use of the fact that the skin is very close to the anterior surfaces of both of these bone structures with minimal intervening flesh, so that the relative anterior/posterior locations of these bone structures accurately represents the relative anterior-posterior locations of the proximal tibia and distal femur.

In each of the four forms of the invention an elongated reference arm has a distal end that is oriented or fulcrumed against a distal region on the tibia, and has a proximal end that either rests on the tibial tubricle or on the patella; while a second reference structure that is movable relative to this reference arm rests against the other of these two anterior bone structures proximate the knee. Displacement indicator means operatively associated with these two reference structures indicates the relative positons of the proximal tibia and distal femur in the anterior-posterior direction.

In the first simplified form of the invention the reference arm has a distal reference pad which rests against a distal region on the tibia and a proximal reference pad which rests against the tibial tubricle, the arm extending proximally from the latter so as to overlie the patella. The second reference structure in this form of the invention is a displacement indicator rod slidably mounted near the proximal end of the reference arm, with a patella reference pad on the posterior end of the rod and a displacement indicator scale along the length of the rod and readable against the reference arm. The second simplified form of the invention is similar to the first simplified form, except that the proximal reference pad on the elongated reference arm is a patellar reference pad, and the displacement indicator rod has the tibial tubricle reference pad on its posterior end. With each of these two simplified forms of the invention for a passive anterior drawer test an anterior force is manually applied to the back of the calf under the tibial tubricle, while a posterior force is applied to the patellar reference pad to hold the patella securely against the femur and to prevent the femur from rising. A passive posterior drawer test is accomplished by manually applying a posterior force against the tibial tubrical reference pad. Thus, while the displacement indicator provides an objective reading of the displacement, nevertheless the force that is applied in testing with these two simplified forms of the invention is up to the feel and experience of the tester, and to that extent is subjective.

In the third form of the invention, which is of intermediate complexity, the second reference structure, instead of being a displacement indicator rod, is a second elongated reference arm that is pivotally connected to the other reference arm; i.e., in this form of the invention the two reference structures are a pair of distally pivotally connected reference arms. The shorter of these two arms is a tibial tubricle reference arm and is formed as a main case of the apparatus; while the longer of the two arms is a patellar reference arm. In this form of the invention the relative angular pivotal positions of the two reference arms is transduced to a displacement indicator dial that has a zeroing adjustment capability so that it can provide a direct readout of anterior or posterior drawer shift without requiring a difference calculation as is required in the two simplified forms of the invention. This third form of the invention still requires a hand-applied anterior force to the calf for a passive anterior drawer test, and a hand-applied posterior force to the tibial tubricle reference arm for a passive posterior drawer test, and is therefore subjective insofar as the amount of the applied force is concerned.

The fourth and most complex form of the invention disclosed herein, like the third form, has a pair of distally pivotally connected reference arms which respectively carry the tibial tubricle reference pad and the patellar reference pad. However, the two reference arms are pivotally connected at their common pivot axis to a case that is adapted to be strapped against the anterior surface of the tibia. A force-applying handle projects above or anterior to the case, and a force-indicating transducer is operatively arranged between the handle and the case to audibly indicate when specific predetermined force levels are applied either anteriorly to the calf under the tibia or posteriorly to the tibia, for making respective anterior and posterior drawer tests. As in the third form of intermediate complexity, the relative angular pivotal positions between the tibial and patellar reference arms is directly readable on a displacement indicator dial, so that with the addition of the force indicating transducer the fourth form of the invention is objective in all respects, including both displacement indicating and force indicating.

A novel posterior thigh support platform forming a part of the present invention is utilized with all four forms of the invention in making anterior drawer tests. This posterior thigh support platform automatically establishes the knee flexion angle within the preferred range of from approximately 20° to approximately 30°, and allows the patient to relax both legs on a stable support surface, avoiding the necessity for the examiner to pick up and manually support the patient's knee, and thereby avoiding the difficulties that were encountered with the Lachman test with obese patients or large athletes, or if the examiner had small hands.

A novel foot positioning platform having both a horizontal footrest and upright lateral foot supports also forms a part of the present invention. This foot positioning platform supports both feet against external rotation, thereby keeping the starting rotational angle of the tibia the same in both knees for a more precise and reliable comparison of both knees with any of the four forms of the invention disclosed herein.

BRIEF DESCRIPTION OF THE DRAWINGS

These and other objects and advantages of the invention will become more apparent from the following description taken in conjunction with the drawings, wherein:

FIG. 7 is a perspective view illustrating the fourth and most complex form of the invention disclosed herein;

FIG. 8 is a an enlarged, fragmentary top plan view of the form of the invention shown in FIG. 7, with the top section of the case removed from the bottom section of the case and turned over so that its underside faces upwardly;

FIG. 9 is a vertical section taken on the line 9—9 in FIG. 8;

FIG. 10 is a fragmentary vertical section taken on the line 10—10 in FIG. 8;

FIG. 11 is a fragmentary vertical section taken on the line 11—11 in FIG. 8;

FIG. 12 is fragmentary horizontal section taken on the line 12—12 in FIG. 11;

FIG. 13 is a diagrammatic view illustrating the electrical circuitry of the force transducer of the fourth form of the invention;

FIG. 14 is a side elevational view similar to FIGS. 2 and 3 but with the fourth form of the invention operatively positioned on the leg;

FIG. 15 is an enlarged, fragmentary side elevational view of the encircled region in FIG. 14 showing the joint line reference arrow;

FIG. 19 is a fragmentary saggital section with the knee at approximately 25° of flexion in preparation for an active anterior drawer test, but prior to contraction of the quadriceps muscles;

FIG. 20 is a view similar to FIG. 19, but with the quadriceps muscles contracted;

FIG. 21 is a fragmentary saggital section with the knee joint at a neutral flexion angle of from about 70° to about 90° for an active posterior drawer test, FIG. 21 showing the tibia/femur relative positioning either for a normal knee or with the quadriceps contracted;

FIG. 22 is a view similar to FIG. 21, but for a knee with a torn posterior cruciate ligament and with the quadriceps relaxed;

DETAILED DESCRIPTION

Figure 1:
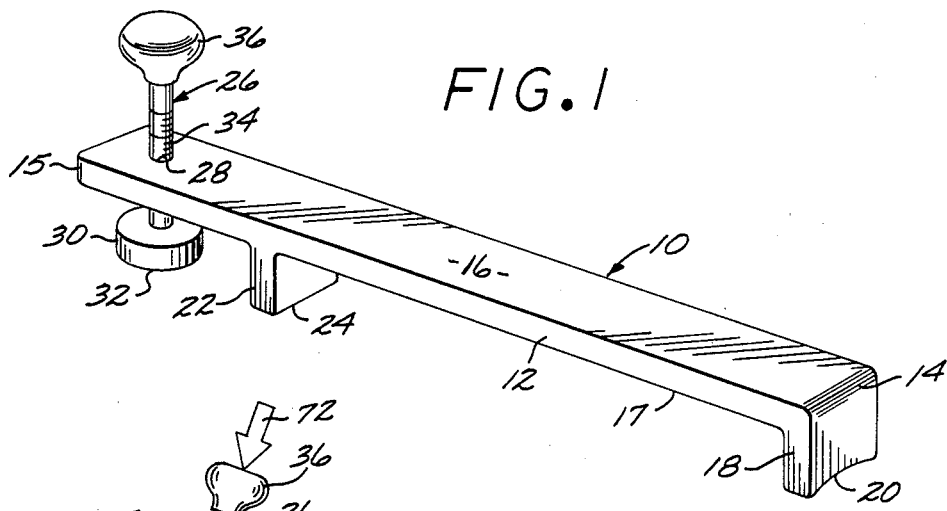
FIG. 1 is a perspective view illustrating the first simplified form of the invention.
Figure 2:
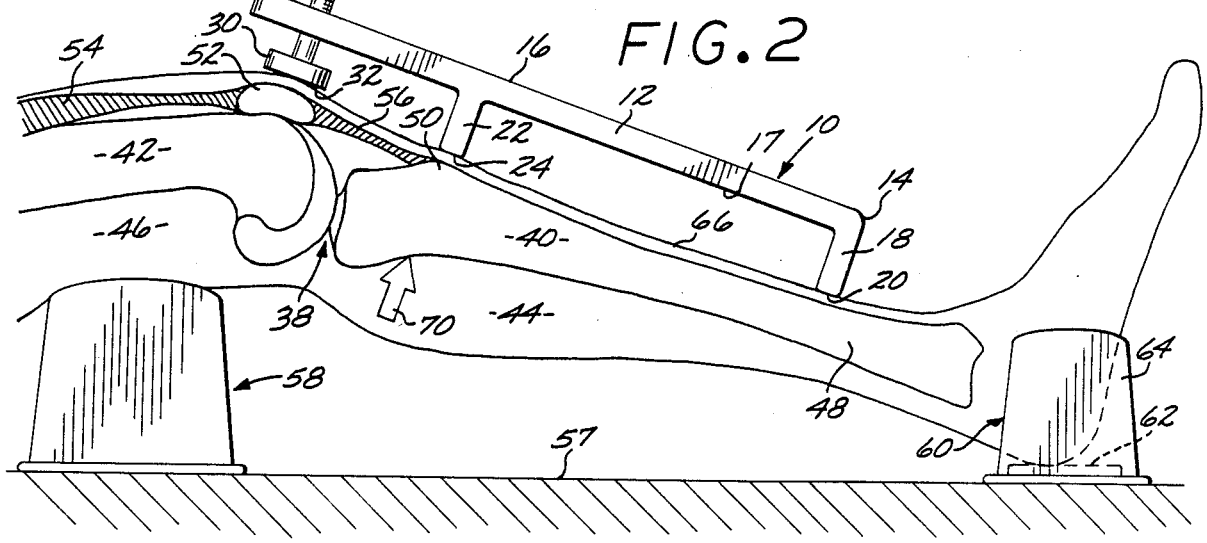
FIG. 2 is a side elevational view of the form of the invention shown in FIG. 1, operatively positioned upon a leg that is shown in sagittal section, with the posterior region of the thigh resting upon the raised posterior thigh support platform of the invention, and with the foot located on the foot support platform of the invention.
Figure 3:
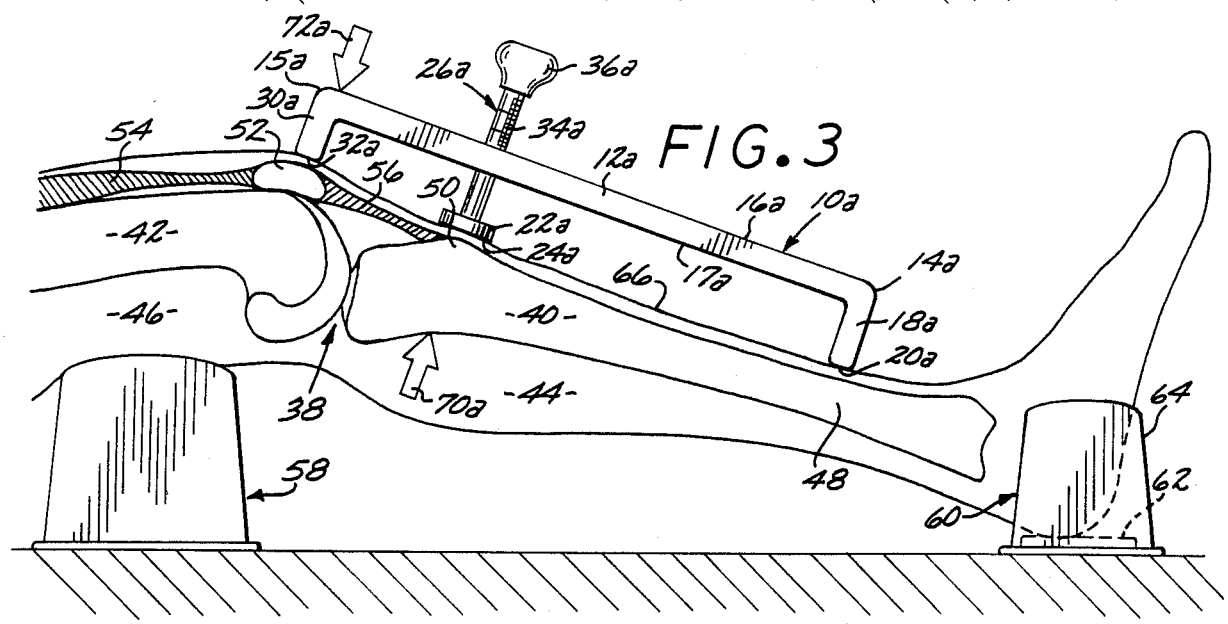
FIG. 3 is a view similar to FIG. 2, but with the second simplified form of the invention operatively positioned on the leg.

FIGS. 1 and 2 illustrate one simplified tibia-referenced knee testing device according to the invention, and FIG. 3 shows another. Each of these two simplified forms of the invention embodies a single reference arm, and both of these forms are adapted for direct hand application of the anterior or forward testing force to the calf behind the tibial tubricle.

The first simplified form of the invention shown in FIGS. 1 and 2 is generally designated 10, and its principal structural element is an elongated, generally flat and preferably straight reference arm 12. The reference arm 12 has distal tibial end 14 and femoral end 15. For clarity and convenience in the following description, the reference arm 12 will also be designated as having an upper or anterior surface 16 and a lower or posterior surface 17.

Projecting downwardly from the reference arm 12 proximate its distal tibial end 14 is a distal tibial reference pad 18, the lower surface of which constitutes the distal tibial reference surface 20 of the device 10. Referencing of the device 10 to the tibia is completed by means of a proximal tibial reference pad 22 that projects downwardly from reference arm 12 at a location spaced proximally from the distal tibial reference pad 18 and located closer to the femoral end 15 than the distal tibial end 14 of reference arm 12. The bottom surface of proximal tibial reference pad 22 constitutes the proximal tibial reference surface 24 of the device 10. The two tibial reference pads 18 and 22 preferably project downwardly at right angles from the main body of the reference arm 12.

Relative positioning and displacement between the tibia and the femur in the anterior-posterior direction is indicated on a displacement indicator rod 26 that is slideably mounted in a bore 28 extending in the anterior-posterior direction through reference arm 12 preferably at right angles to the arm 12. Mounted on the lower end of indicator rod 26 is a patellar reference pad 30, the bottom surface 32 of which constitutes the patellar reference surface of the knee testing device 10. Actually, the reference pad 30 and its bottom reference surface 32 are for the purpose of referencing the anterior-posterior location of the distal end of the femur; however, the reference pad 30 and its reference surface 32 perform such femoral referencing through the patella which is the only stable, generally unyielding structure proximate the knee that is accessible for referencing the location of the distal end of the femur. Displacement indicator rod 26 and proximal tibial reference pad 22 are spaced apart longitudinally along the reference arm 12 a distance approximating the average spacing between patella 52 and tibial tubricle 50.

The displacement indicator rod 26 has an indicator scale 34 longitudinally arranged thereon which is adapted to be read at the upper surface 16 of reference arm 12. A knob 36 is mounted on the upper end of displacement indicator rod 26 for receiving a posteriorly directed stabilization counterforce during a passive anterior drawer test.

FIG. 2 shows the knee testing device 10 operatively positioned on a leg for performing the passive anterior drawer test. The leg is diagramatically illustrated, with the knee joint 38 shown generally in sagittal section. The leg is supported for this passive anterior drawer test with the knee joint 38 bent or flexed to a preferred flexion angle in the range of from about 20° to about 30° of flexion, and preferably at approximately 25° of flexion, to minimize interference by ligaments and other knee components not involved in the test, and by hamstring guarding, as described more in detail hereinafter. This knee joint flexion angle represents angular displacement between the general longitudinal axes of the tibia 40 and femur 42 from the fully extended condition of the leg, the tibia 40 being the anterior and larger of the two long bones of the calf 44, and the femur 42 being the single long bone extending through the thigh 46.

The knee testing device 10 is placed against the anterior surface of the leg with the reference arm 12 arranged generally parallel to the tibia 40, the distal tibial reference surface 20 engaged at a distal region 48 of the tibia, the proximal tibial reference surface 24 engaged at the tibial tubricle 50, and the patellar reference surface 32 engaged at the patella 52. The patella 52 serves as a bearing for force applied by the quadraceps muscles 54 against the distal end of the femur 42, the quadraceps 54 all coming in and attaching to the patella 52 and thence through the patella 52 and the patellar tendon 56 (which is really a ligament) to the tibial tubricle 50. An anatomical factor in knee functioning which enables the present invention in all of its forms to be basically tibia referenced while also referencing to the patella is the fact that the patella slides distally and posteriorly on the curved lower end of the femur so that the patella is fully exposed on the femur in the general anterior direction of the tibia at any knee flexion angle up to and even beyond 90° of flexion. Thus, the patella 52 is exposed as a reference point for anterior drawer tests with flexion angles ranging from about 20° to about 30° and also for posterior drawer tests with flexion angles ranging from about 70° to about 90°.

To perform the passive anterior drawer test as illustrated in FIG. 2, the patient is preferably fully supported from head to foot on a firm horizontal surface 57. The knee joint 38 is stabilized for the test by placement of a raised posterior thigh support platform 58 under the thighs proximal to the patient's patella 52. Further stabilization of the knee joint 38 is accomplished by means of a foot support platform 60 which has a horizontal foot rest 62 preferably covered with foam rubber or neoprene and a pair of upright lateral foot supports 64 at opposite sides of the platform 60. The raised posterior thigh support platform 58 automatically establishes the desired knee flexion angle within the preferred range of about 20° to 30°, and keeps this knee flexion angle constant throughout the test for accuracy of measurement. The foot support platform 60 supports the foot against external rotation which might otherwise interfere with the reliability and repeatability of the tests. Since most tests utilizing the present invention involve a comparison of the tibia-femur displacement of the injured knee with that of the uninjured knee, both of the thighs are supported on the raised thigh support platform 58 and both of the feet are supported by the foot support platform 60.

The tibia 40 provides an almost ideal base or referencing structure for the tibia-referenced system of the invention because the skin 66 is very close to the anterior surface of tibia 40, both in the distal region 48 thereof and at the tibial tubricle 50, with minimal intervening flesh.

To perform a passive anterior drawer test, the knee testing device 10 is operatively positioned as shown in FIG. 2 and the reading on displacement indicator scale 34 is noted and preferably recorded. An anterior-directed testing force is then applied, preferably with the right (or dominant) hand, to the back of the calf 44 behind tibial tubricle 50 as indicated by the arrow 70. As discussed in detail hereinafter, this anterior-directed force 70 is preferably about 20 pounds of force; however, since the simplified form 10 of the invention does not embody any force indicating means, the amount of this force will be up to the feel and experience of the tester, and therefore will be somewhat subjective. During this application of the anterior force 70, a posterior-directed stabilization counterforce is applied to the top of the force knob 36 as indicated by the arrow 72 to keep the entire knee and thigh firmly against the posterior thigh support platform 58, thereby blocking the tendency of the leg to lift off of the thigh support platform 58 during the test, which would cause the knee joint to flex and introduce an error in the measurement. The displacement indicator scale 34 is again read and preferably recorded while the force 70 and counterforce 72 are applied, and the difference between these two indicator scale readings will constitute a measurement of the anterior drawer shift or displacement of the tibial tubricle 50 relative to the patella 52, and hence relative to the distal end of femur 42. Preferably, the readout on displacement indicator scale 34 is directly in millimeters of anterior drawer shift or displacement at the knee joint line. Because the length from the fulcrum of distal tibial reference pad 18 to displacement indicator rod 26 is approximately 10 percent greater than the length from pad 18 to the knee joint line, the actual scale of displacement indicator scale 34 is expanded by approximately 10 percent from a true metric scale to give this direct readout in millimeters of drawer shift.

Accuracy of this anterior drawer test made with the knee testing device 10 may be slightly improved by applying the posterior stabilization force 72 and taking the first reading on the displacement indicator scale 34 prior to application of the anterior force 70. This causes the patellar reference pad 30 to seat firmly upon the skin 66 overlying the patella 52 and assures that the patella 52 is firmly seated in the femoral notch; otherwise, such seatings might occur between the two displacement indicator scale readings and introduce an error in the reading.

Figure 17:
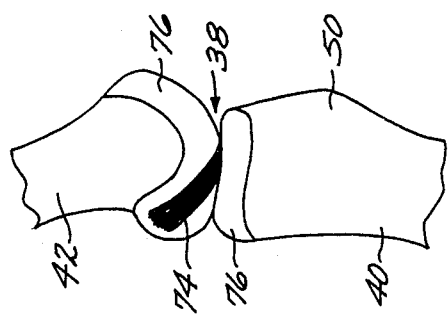
FIG. 17 is a view similar to FIG. 16, but with the knee at a flexion angle of 25°, illustrating the location of the anterior cruciate ligament.

The passive anterior drawer test is for the purpose of testing the laxity of the anterior cruciate ligament. Referring to FIG. 17 of the drawings, the anterior cruciate ligament is generally designated 74, and its position in the knee joint 38 is illustrated for a knee flexion angle of 25°, which is the preferred testing angle for the anterior drawer test. It will be seen that the anterior cruciate ligament 74 comes from the posterior notch of the femur 42 and runs to the anterior plateau of the tibia 40. The anterior cruciate ligament 74 resists the tendency of the tibia 40 to slide forwardly relative to the femur 42. Cartilage surfaces at the ends of the tibia 40 and femur 42 are generally designated 76.

Figure 16:
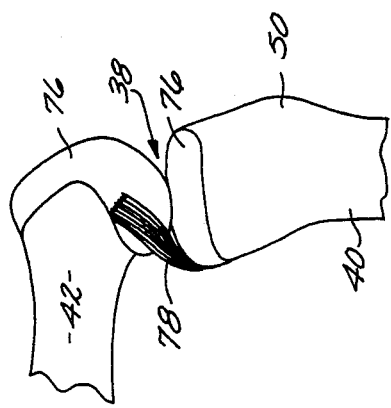
FIG. 16 is a fragmentary saggital section of the knee joint at 90° of flexion showing the location of the posterior cruciate ligament.

FIG. 16 shows the posterior cruciate ligament, generally designated 78, with the knee joint 38 at 90° of flexion, which is the preferred knee flexion for performing a posterior drawer test. Such test will be described later. It will be seen that the posterior cruciate ligament 78 comes out of the distal end of the femur 42 and runs posterior to the tibia 40. The posterior cruciate ligament 78 mechanically functions as one of the stabilizers resisting posterior displacement of the tibia 40 relative to the femur 42.

The other cruciate ligament is not shown in each of the illustrations in FIGS. 16 and 7 for clarity of illustration.

Referring now to FIG. 3 of the drawings, the second simplified form of the invention is generally designated 10a, and it has as its principal structural element an elongated and preferably generally flat reference arm 12a having distal tibial end 14a, femoral end 15a, upper or anterior surface 16a, and lower or posterior surface 17a. The distal tibial reference pad 18a is the same as the reference pad 18 of the first form 10 shown in FIGS. 1 and 2, extending downwardly or posteriorly from the distal tibial end 14a of reference arm 12a preferably at right angles to arm 12a. The bottom surface of distal tibial reference pad 18a constitutes the distal tibial reference surface 20a of the device 10a.

Integral with the reference arm 12a and projecting downwardly from its femoral end 15a preferably at right angles to arm 12a is the patellar reference pad 30a, the bottom surface of which constitutes the patellar reference surface 32a of the device 10a. Thus, the reference arm 12a directly references the anterior-posterior locations of the distal region 48 of tibia 40 and the patella 52; whereas the reference arm 12 of the device 10 of FIGS. 1 and 2 directly references the distal region 48 of tibia 40 and the tibial tubricle 50.

In the knee testing device 10a of FIG. 3, the proximal tibial reference pad 22a, the lower surface of which is the proximal tibial reference surface 24a, is mounted or formed integrally on the lower end of the displacement indicator rod 26a which is slideably mounted in a suitable bore (not shown) through arm 12a for sliding movement in the anterior-posterior direction. Preferably, the rod 26a has its longitudinal axis directed at right angles to the arm 12a. The displacement indicator rod 26a is spaced longitudinally along the reference arm 12a from patellar reference pad 30a a distance approximating the average spacing between tibial tubricle 50 and patella 52.

The knee testing device 10a is operatively positioned as illustrated in FIG. 3, with the distal tibial reference surface 20a against the skin at the distal region 48 of the tibia, the patellar reference surface 32a against the skin at the patella 52, and the proximal tibial reference surface 24a against the skin at the tibial tubricle 50. With the device 10a thus located, the displacement indicator scale 34a on rod 26a is read and preferably recorded. Then, the anterior-directed displacement force indicated by the arrow 70a is applied to the back of calf 44, preferably with the right (or dominant) hand of the tester, while the posterior-directed stabilization counterforce indicated by the arrow 72a is applied to reference arm 12a proximate the patellar reference pad 30a with the left (or non-dominant) hand of the tester. While these forces 70a and 72a are being applied, the displacement indicator scale 34a is again read relative to the upper surface 16a of arm 12a, and this reading preferably recorded, and the difference between the two readings on indicator scale 34a will directly provide the amount of anterior drawer shift or displacement of tibia 40 relative to patella 52 and hence the distal end of femur 42, in millimeters of displacement. Because the length from the fulcrum of distal tibial reference pad 18a to displacement indicator rod 26a is approximately 10 percent less than the length from pad 18a to the knee joint line, the actual scale of displacement indicator scale 34a is shrunk by approximately 10 percent from a true metric scale to give this direct readout in millimeters of drawer shift.

The second simplified form 10a of the invention shown in FIG. 3, like the first form shown in FIGS. 1 and 2, may be employed in other knee ligament tests, such as posterior drawer tests, that will be described below for all of the embodiments of the invention shown and described herein.

Figure 4:
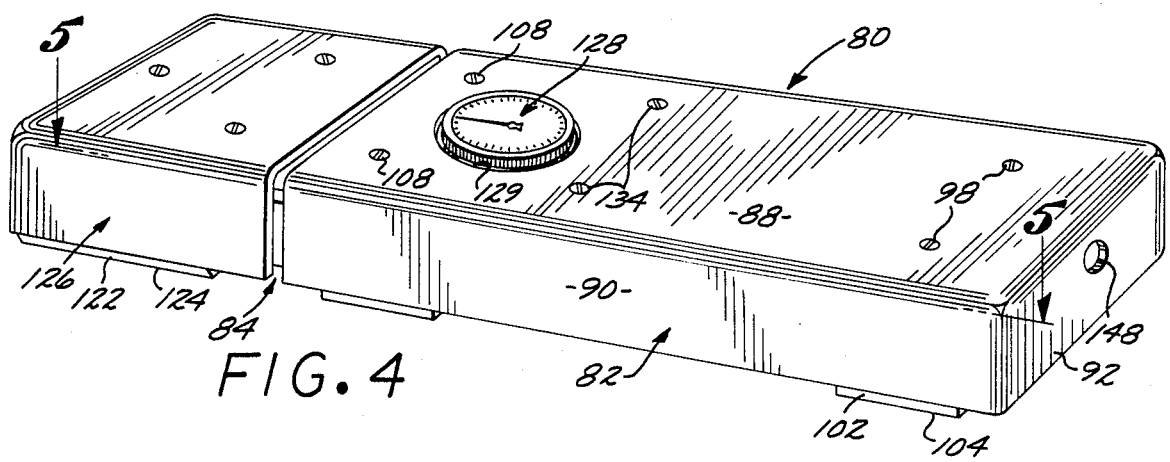
FIG. 4 is a perspective view illustrating the third form of the invention which is of intermediate complexity.
Figure 5:
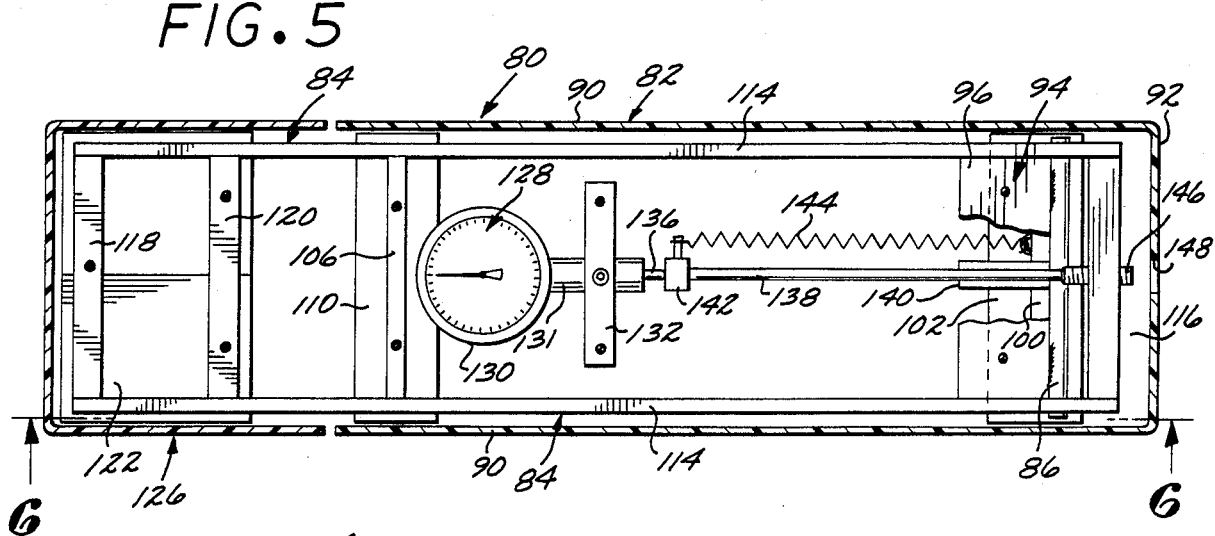
FIG. 5 is a horizontal section taken on the line 5—5 in FIG. 4.
Figure 6:
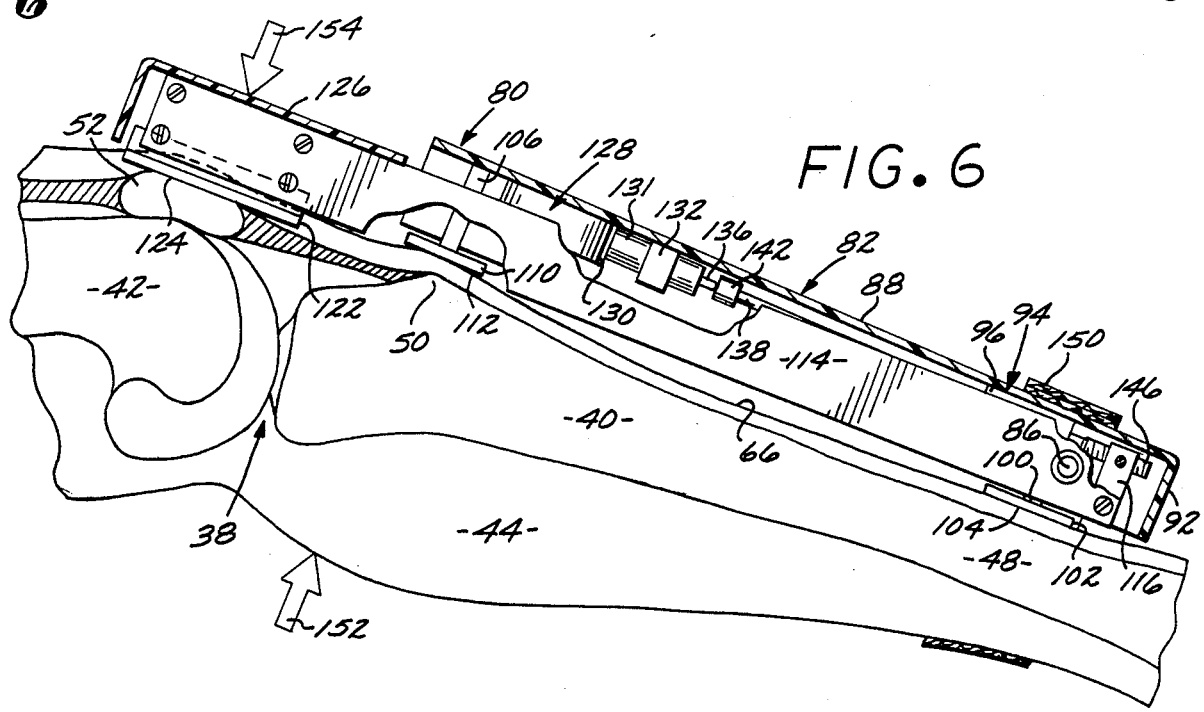
FIG. 6 is a vertical section taken on the line 6—6 in FIG. 5 and illustrating the third form of the invention applied to a leg that is shown in saggital section.

FIGS. 4 to 6 of the drawings illustrate a third form of the invention, generally designated 80, which is of intermediate complexity, embodying two pivotally connected reference arms which respectively carry the tibial tubricle reference pad and the patellar reference pad. Relative pivotal motion between these two reference arms is utilized to actuate a displacement dial indicator that provides a direct reading of drawer shift between tibia and femur without requiring the difference calculation associated with the displacement indicator scales of the simpler forms of the invention shown in FIGS. 1 to 3. The knee testing device of FIGS. 4 to 6 still requires hand application of the anterior-directed testing force to the calf behind the tibial tubricle.

The knee testing device 80 has a tibial reference arm 82 in the form of the main case of the device, and a patellar reference arm generally designated 84, the two reference arms 82 and 84 being pivotally interconnected proximate their distal ends by means of a transverse pivot shaft 86. The tibial reference arm (main case) 82 carries distal and proximal tibial reference pads near its respective ends, while the patellar reference arm 84 carries a patellar reference pad near its proximal, free end.

The tibial reference arm case 82 includes an elongated, flat top or anterior wall 88, a pair of elongated, straight, parallel side walls 90 extending downwardly or posteriorly from the top wall 88, and a tibial distal end wall 92. The side walls 90 serve as longitudinal structural rails or beams of the tibial reference arm 82.

A generally L-shaped support block 94 extends transversely across the inside of case 82 and has a generally flat upper plate portion 96 which is attached to the top wall 88 by means of screws 98. A downwardly extending plate portion 100 of support block 94 extends downwardly from the distal edge of upper plate portion 96 and has the distal tibial reference pad 102 attached to or formed on its lower edge. The bottom surface of reference pad 102 constitutes the distal tibial reference surface 104 of the device 80. The transverse pivot shaft 86 is rigidly secured to the distal side of support plate portion 100, as by welding or brazing.

A proximal tibial reference pad support plate 106 is attached to the top wall 88 of case 82 by means of screws 108, the plate 106 extending downwardly or posteriorly from top wall 88 and having proximal tibial reference pad 110 attached to or formed on its lower end, the bottom surface of reference pad 110 constituting the proximal tibial reference surface 112. Both of the tibial reference pads 102 and 110 are displaced slightly below the lower edges of the case side walls 90 to avoid interference by the main case 82 during testing operations.

The patellar reference arm 84 consists of a pair of parallel longitudinal structural rails or beams 114, a transverse brace 116 connecting the rails 114 together at their distal tibial ends, a transverse brace 118 connecting the rails 114 together at their patellar end, and another transverse brace 120 being connected between the rails 114 a short distance distally of the brace 118. Patellar reference pad 122 is attached to the lower edges of the cross braces 118 and 120, and its bottom surface constitutes the patellar reference surface 124. The patellar reference pad 122 is preferably shaped as an inverted V with its apex directed longitudinally of the testing device 80 to assure lateral centering of the reference pad 122 over the patella 52. Thus, in FIG. 6 the upper part of patella 52 is seen recessed into this inverted V of the patellar reference pad 122.

The portion of patellar reference arm 84 exposed proximally of the tibial reference arm case 82 is provided with a patellar cover 126 which is contoured to appear as an extension of the main case 82 and gives the entire knee testing device 80 an attractive and professional appearance. The cover 126 is attached to the pair of cross braces 118 and 120.

The indicating mechanism which provides a direct readout of the drawer shift of the tibia relative to the femur during a test will now be described. The displacement dial indicator is generally designated 128, and is supported in a circular opening 129 in the main case top wall 88 at a convenient location for viewing near the proximal end of top wall 88. The displacement dial indicator 128 has a generally cylindrical casing 130 from which a sleeve 131 projects in the axial, distal direction of the device 80. The sleeve 131 extends through and is secured to a support block 132 which, in turn, is connected to the underside of the case top wall 88 by means of screws 134. Thus, the support block 132 and sleeve 131 support the displacement dial indicator 128 in its operative position. A displacement indicator actuator pin 136 projects axially from the distal end of sleeve 131.

A push rod 138 is axially slideably supported in an axially oriented bushing 140 that is fixedly mounted in the plate portion 100 of support block 94. A connector block 142 connects the proximal end of push rod 138 to the dial actuator pin 136. A tension spring 144 is connected between the block 142 and plate 100 of support block 94 so as to bias the push rod 138 and dial actuator pin 136 in the distal direction to a position adjustably determined by an adjustment screw 146 that is mounted in the transverse brace 116 at the distal end of patellar reference arm 84. Adjustment screw 146 is substantially axially aligned with push rod 138, and both adjustment screw 146 and push rod 138 are displaced upwardly from the axis of pivot shaft 86. Because the push rod 138 and the displacement dial indicator 128 which it actuates are mounted on the tibial reference arm 82 while the adjustment screw 146 is mounted on the patellar reference arm 84, relative pivoting movement between the reference arms 82 and 84 will cause the adjustment screw 146 to impart axial movement to push rod 138 that is indicated on the displacement dial indicator 128.

Thus, as best seen in FIG. 6, when the proximal tibial reference pad 112 on tibial reference arm 82 is raised relative to the patellar reference pad 122 on patellar reference arm 84, the resulting clockwise pivoting (in FIG. 6) of tibial reference arm 82 relative to patellar reference arm 84 causes the push rod 138 to be slideably shifted in its mounting on tibial reference arm 82 to the left or in the proximal direction, producing a proportional amount of movement of the displacement dial indicator 128. Conversely, a lowering or posterior movement of proximal tibial reference pad 110 relative to patellar reference pad 122 and consequent anti-clockwise pivoting movement of tibial reference arm 82 relative to patellar reference arm 84 will cause the mounting structure for push rod 138 and dial indicator 128 to be displaced to the left in FIG. 6 relative to adjustment screw 146, allowing the spring 144 to shift the push rod 138 and dial actuator pin 136 to the right on tibial reference arm 82 so as to move displacement dial indicator 128 in the opposite direction.

An adjustment screw access hole 148 is provided in end wall 92 of case 82 to enable a one-time factory zeroing adjustment of screw 146 to be made to set the indicator needle of displacement dial indicator 128 at approximately the 12:00 o'clock position for the average person. Final zeroing at the beginning of each test is accomplished by directly rotating the preferably circumferentially knurled dial itself relative to the indicator needle. FIG. 6 shows the testing device 80 operatively located on the anterior surface of a leg for an anterior drawer test. The main case 82 is strapped against the shin by wrap-around distal strap 150 which holds the distal tibial reference pad 102 securely against the distal tibial region 48 and also secures the proximal tibial reference pad 110 and patellar reference pad 122 in their correct axial locations overlying the tibial tubrical 50 and the patella 52, respectively. Preferably, the wrap-around strap 150 is releasably secured with "Velcro." With the testing device 80 thus located for making a passive anterior drawer test, the dial of displacement indicator 128 is rotatably adjusted to the zeroed reference position. Then an anterior-directed force 152 is applied to the back of the calf 44 and a posterior-directed counterforce 154 is applied against the top of the patellar pad cover 126, and the anterior drawer shift or displacement of the tibial tubricle 50 relative to the patella 52, and hence relative to the distal end of femur 42, will be read out directly in millimeters of displacement on the displacement dial indicator 128.

FIGS. 7 to 14 illustrate a fourth embodiment of the invention which is generally designated 160 and is the most complex form of the invention that is specifically shown and described herein. Like the third form of the invention shown in FIGS. 4 to 6, the fourth form 160 has two pivotally interconnected reference arms. However, unlike any of the other forms, the testing device 160 has a separate case to which the reference arms are pivoted that is adapted to be strapped against the front of the tibia, with a force-applying handle above or anterior to the case and a force-indicating transducer operatively connected between the handle and case to indicate when predetermined force levels are applied to a proximal region of the tibia, either anteriorly by pulling up on the handle or posteriorly by pushing down on the handle.

The case is generally designated 162, and is composed of separate elongated lower (posterior) and upper (anterior) sections 164 and 166, respectively, which are releaseably connected together at an overlapping joint 167 for assembly and adjustment of internal parts. The tibial and patellar reference arms are generally designated 168 and 170, respectively, and they are coaxially pivotally mounted on a pivot shaft 172 that is transversely supported in a support block 174 affixed to the generally flat central bottom wall section 176.

The distal tibial reference pad 178 is formed as a part of the lower section 164 of case 162, projecting downwardly or posteriorly below the generally flat central section 176 of the bottom wall at the distal end of lower case section 164. The bottom surface of reference pad 178 constitutes the distal tibial reference surface, and this surface is preferably padded with a thin layer of foam rubber or neoprene for the comfort of the patient. The cupped inside of distal tibial reference pad 178 provides a battery mounting cavity 182 within which a battery 184 is supported for providing electrical energy to the force-indicating transducer.

A proximal tibial case locator pad 186 is also formed as a part of the lower case section 164, projecting downwardly or posteriorly below and proximally of the generally flat central bottom wall section 176. As seen in FIG. 14, the case locator pad 186 is adapted to engage the front of tibia 40 just distally of the tibial tubricle 50, while the distal tibial reference pad 178 is adapted to engage against the front of tibia 40 at the more remote distal region 48 of tibia 40. The proximal case locator pad 186 preferably has an inverted V configuration similar to that of the patellar reference pad 122 of device 80 of FIGS. 4–6, and is also preferably padded with a thin layer of foam rubber or neoprene.

As best seen in FIG. 8, the tibial reference arm 168 consists of a pair of longitudinally arranged, laterally spaced, parallel, elongated rails or beams 188 that are connected near their proximal ends by a transverse brace 190 which serves as the support for the proximal tibial reference pad 192, the pad 192 being mounted or formed on the lower edge of brace 190. The bottom surface of reference pad 192 constitutes the proximal tibial reference surface 194. The distal ends of the longitudinal rails 188 of tibial reference arm 168 are pivotally mounted on the pivot shaft 172.

The longitudinal structural members of the patellar reference arm 170 are a pair of long, parallel, longitudinally arranged rails or beams 196 which are connected by a transverse brace 198 at their distal ends and connected by a transverse block 200 at their proximal or patellar ends. The patellar reference pad 202, the bottom surface of which forms the patellar reference surface 204, is mounted on the lower end of an adjustment slide generally designated 206 which serves as a zeroing device to compensate for differing heights of patellas. The adjustment slide 206 includes a pair of parallel rods 208 that are oriented in the anterior-posterior direction, a lower cross-block 210 to which the lower ends of rods 208 are connected, and an upper cross-block 212 to which the upper ends of rods 208 are connected. The patellar reference pad 202 is attached to the lower cross-block 210, while a counterforce application pad 214 is attached to the upper cross-block 212. A transverse set screw 216 is threadedly mounted in the transverse block 200 and engageable against one of the rods 208 to releaseably lock the adjustment slide 206 in a position of adjustment for a particular patient.

As best shown in FIGS. 14 and 15, a joint line reference arrow 218 is located on at least one of the pair of longitudinal rails 196 forming a part of patellar reference arm 170 to aid the user of the knee testing device 160 in properly locating the device 160 on the tibia with the proximal tibial reference pad 192 and the patellar reference pad 202 properly registering with tibial tubricle 50 and patella 52, respectively. As seen in FIG. 14, the testing device 160 is mounted on the tibia 40 so that the arrow 218 is directed as closely as possible toward the joint line 219 of knee joint 38. The testing device 160 has a displacement dial indicator 220 that is calibrated to read out directly in millimeters of drawer shift when the arrow 218 is positioned so as to be directed at the joint ine 119. Thus, proper location of arrow 218 at joint line 119 assures that the testing device 160 is operating at its calibration point for the displacement readout. It also assures that a correct, predetermined mechanical advantage at the joint line 219 of the anterior or posterior force that is applied to the case 162 as described hereinafter.

The displacement dial indicator 220 is mounted in the upper case section 166, preferably near the proximal end of case section 166, with the face of dial indicator 220 visible from above. The displacement dial indicator 220 is actuated in a manner generally similar to the displacement dial indicator 128 of the form of the invention shown in FIGS. 4 to 6, but by different means because of the fact that the case 162 upon which the dial indicator 220 is mounted is not itself one of the two reference arms which pivot relative to each other. Thus, actuation of the displacement dial indicator 220 in the fourth form of the invention shown in FIGS. 7 to 15 is accomplished through a push-pull flexible cable generally designated 222, rather than through the push-pull rod mechanism of the third form of the invention shown in FIGS. 4 to 6.

The flexible cable 222 includes a flexible, resilient and non-extensible outer referencing sheath 224 and an inner stranded flexible cable 226 which slides longitudinally within the outer sheath 224. The proximal end of cable sheath 224 is clamped within a cable mounting block 228 that is affixed on the upper case section 166 as seen in FIG. 8. A distal cable mounting block 230 is rigidly affixed to one of the longitudinal rails 188 of tibial reference arm 168 as seen in FIGS. 8 and 10, and the distal end of cable sheath 224 is longitudinally adjustably clamped in the block 230 at a location offset upwardly or anteriorly relative to the pivot shaft 172. The distal end of inner sliding cable 226 is longitudinally adjustably clamped to the transverse brace 232 of patellar reference arm 170 by means of a clamp block 232, the clamped location of the distal end of inner cable 226 also being offset upwardly or anteriorly relative to the pivot shaft 172 at approximately the same level as the clamped location of the distal end of cable sheath 224. The proximal end of inner sliding cable 226 is coupled to the actuator pin 234 of displacement dial indicator 220 by means of a connector block 236, and the inner cable 226 and dial actuator pin 234 are biased generally in the proximal direction for stabilization by means of a tension spring 238 engaged between the dial indicator 220 and the connector block 236.

Because the clamped distal ends of the outer and inner cable elements 224 and 226, respectively, are offset upwardly from the pivot shaft 172, a raising or clockwise angular movement of tibial reference arm 168 relative to patellar reference arm 170 produces a proportional closing movement of the blocks 230 and 232 toward each other, sliding the inner cable 226 generally proximally toward the displacement dial indicator 220 and shifting the dial actuator pin 234 so as to move dial indicator 220 in one direction. Conversely, a lowering or anti-clockwise angular movement of tibial reference arm 168 relative to patellar reference arm 170 produces a proportional opening movement of blocks 230 and 232 away from each other, sliding the inner cable 226 generally distally away from dial indicator 220 and shifting dial indicator pin 234 so as to move dial indicator 220 in the opposite direction. Thus, the offset above pivot shaft 172 of the flexible cable components 224 and 226 at their distal ends converts pivotal displacement between the respective tibial and patellar reference arms 168 and 170 back to translational displacement that is representative of the translational displacement between the proximal end of the tibia and the patella, and this is displayed on the displacement dial indicator 220.

The case 162 has two wrap-around straps attached to it for supporting the case on the tibia at the locations shown in FIG. 14. One of these is a distal strap 240 that is located generally in longitudinal registry with the distal tibial reference pad 178, and the other is a proximal strap 242 which is located generally in longitudinal registry with the proximal tibial locator pad 186. These straps 240 and 242 are preferably made of "Velcro," and as shown in FIG. 7, one end portion 243 of each of the straps 240 and 242 is connected to a side of the upper housing section 166 and arranged transversely across the top of the upper case section 166, with the long, free part of the strap adapted to be wrapped around the calf and then back up into overlapping, releaseably attached relationship with the strap portion 243.

The tibial force-applying and indicating mechanisms that are associated with the case 162 will now be described. A force-applying handle 244 is attached to the upper end of a rod 246 that extends downwardly through an opening 247 in the top of upper case section 166 and is connected to the proximal end of a spring beam 248 that is longitudinally arranged in the case 162. The opening 247 is slightly larger than the cross-section of rod 246 to avoid binding; and if desired, rollable bearing means (not shown) may be mounted on upper case section 166 to guide the rod 246 in the opening 247. Handle 244 is preferably oriented transversely to the general longitudinal axis of the case 162 as seen in FIGS. 7 and 14. The lower end of rod 246 is preferably connected to the proximal end of spring beam 248 by means of a single longitudinally oriented screw 250 which allows transverse pivoting movement of rod 246 relative to spring beam 248 to facilitate final assembly of the device 160 and enable the upper case section 166 to be disconnected from the lower case section 164 and tilted to one side for making internal adjustments without disconnecting handle 244 from rod 246 or rod 246 from spring beam 248. This pivotal connection of the handle rod 246 to the spring beam 248 also prevents any twisting torque from being applied to the spring beam 248 upon manipulation of handle 244, which might otherwise introduce errors in the adjustments of the microswitches that are part of the force indicating transducer system. The distal end of spring beam 248 is rigidly secured to the support block 174 in lower case section 164 by a transverse series of screws 252.

With the case 162 of testing device 160 operatively strapped against the tibia as illustrated in FIG. 14, upward or anterior pulling force on the handle 244 will be applied to the case 162 through rod 246, spring beam 248 and support block 174, being applied to the calf 44 through strap 242. This application of the upward force through the spring beam 248 will cause an upward bending deflection of spring beam 248 that corresponds to the amount of upward or anterior force applied to the calf 44, and this upward deflection of spring beam 248 is transduced to audible beeps which provide a quantitative indication of the amount of upward force applied. Conversely, downward or posterior pushing force against the handle 244 is applied to the case through the spring beam 248, being applied to the tibia 40 through the proximal tibial locator pad 186 on case 162 and producing a downward bending deflection of the spring beam 248 that is transduced to audible beeps quantitatively indicating the amount of downward force applied. The transducing system for producing these audible beeps is illustrated in detail in FIGS. 11 to 13.

The transducer preferably employs a two-tone beeper 254 mounted on the proximal end portion of lower housing section 164 as shown in FIG. 8, and two pairs of microswitches mounted under the spring beam 248 on a longitudinal rail or beam 256 that extends in the proximal direction from support block 174 along the central bottom wall portion 176 of lower case section 164. All of the microswitches are normally open and each is arranged to close and complete a circuit from battery 184 to beeper 254 according to a specific pull or push deflection of the spring beam 248.

One pair of microswitches 258 and 258a is responsive to pull deflections of spring beam 248, while a second pair of microswitches 260 and 260a is responsive to push deflections of spring beam 248. The pull-responsive microswitch 258 is arranged to close and produce a first beep at a first pull force preferably of about 15 pounds, while the pull-responsive microswitch 258a is arranged to close and produce a second beep at a second pull force preferably of about 20 pounds. Similarly, the push-responsive microswitch 260 is arranged to close and produce a first beep at a first push force preferably of about 15 pounds, while the push-responsive microswitch 260a is arranged to close and produce a second beep at a second push force preferably of about 20 pounds. Contact actuator screws 262 and 262a mounted on spring beam 248 operatively engage contacts of the respective pull-responsive microswitches 258 and 258a, while contact actuator screws 264 and 264a on spring beam 248 operatively engage contacts of the respective push-responsive microswitches 260 and 260a. Each of the contact actuator screws 262, 262a, 264 and 264a is threadedly adjustable on spring beam 248 for adjustment of the force levels at which the respective microswitches 258, 258a, 260 and 260a are closed.

The diagram of FIG. 13 illustrates the operative relationships between the contact actuator screws and the respective microswitch contacts, and illustrates electrical circuitry suitable for energizing the two-tone beeper 254. Conductors 266 and 268 electrically connect the negative side of battery 184 to the movable contact of each of the microswitches 258, 258a, 260 and 260a. A conductor 270 electrically connects the positive side of battery 284 to a common terminal 272 on beeper 254. Beeper 254 also has respective first and second beep terminals 274 and 276 thereon which, when selectively electrically connected to the negative side of battery 184, cause the beeper 254 to emit respective first (preferably relatively low frequency) and second (preferably relatively high frequency) audible tones or beeps.

In FIG. 13 the contacts of all four microswitches are digramatically illustrated in their open positions for the position of repose of spring beam 248 with no pull or push force applied thereto. The pull microswitches 258 and 258a are normally closed switches, but in the relaxed condition of the testing apparatus as illustrated in FIG. 13, the actuator screws 262 and 262a hold the movable contacts in open positions, with the movable contact of first beep microswitch 258 being held closer to its fixed contact than the movable contact of the second beep microswitch 258a to its fixed contact. Thus, when the spring beam 248 deflects upwardly, carrying the actuator screws 262 and 262a upwardly with it, the initially closer contacts of first beep microswitch 258 will close at a smaller beam deflection than the second beep microswitch 258a. When the contacts of first beep microswitch 258 close they connect the negative conductor 268 to first beep terminal 274 of beeper 254 to cause emission of the first beep from beeper 254, preferably at about 15 pounds of pull force. Then, a further increase in the pull force and further deflection of spring beam 248 and raising of actuator screws 262 and 262a will cause second beep microswitch 258a to close, thereby connecting the negative conductor 268 to second beep terminal 276, causing the beeper 254 to emit the second beep, preferably at about 20 pounds of force.

The push force-responsive microswitches 260 and 260a are normally open microswitches, and with the spring beam 248 in its position of respose, the contacts of first beep microswitch 260 are closer than the contacts of second beep microswitch 260a. Thus, as spring beam 248 deflects progressively further under an increasing push force, carrying the actuator screws 264 and 264a therewith, the contacts of first beep microswitch 260 will be the first to close, connecting negative conductor 266 to first beep terminal 274, preferably at a push force of about 15 pounds. Then, as the push force further increases, the contacts of second beep microswitch 260a will close to connect the negative conductor 266 to second beep terminal 276, preferably at about 20 pounds of push force.

As best seen in FIG. 11, a beam limiting screw 278 protects the microswitches against overtravel of the spring beam 248 in either direction.

Referring to FIG. 14, with the knee testing device 160 strapped against the tibia 40 at the correct longitudinal location as indicated by the joint line arrow 218, the independent pivotal movability of each of the tibial and patellar reference arms 168 and 170, respectively, relative to the case 162 and to each other causes the proximal tibial reference pad 192 to rest against the tibial tubrical 50 under the weight of tibial reference arm 168 and the patellar reference pad 202 to rest against the patella 52 under the weight of the patellar reference arm 170. The adjustment slide 206 to which patellar reference pad 202 is attached is then adjusted in the anterior-posterior direction according to the height of the patella 52 relative to the tibial tubrical 50 of the particular patient so as to approximately zero the reading on the displacement dial indicator 220. Final, more accurate zeroing may then be accomplished by direct rotation of the preferably circumferentially knurled dial itself relative to the indicator needle, and then the device 80 is ready for making the desired test. In FIG. 14, the leg is supported by thigh support platform 58 and foot support platform 60 at the preferred 25° of flexion for an anterior drawer test. To make the passive anterior drawer test, the handle 244 is pulled upwardly or anteriorly, preferably using the right (or dominant) hand, and a downward or posterior stabilization force is applied to the counterforce application pad 214 above patellar reference pad 202, preferably by the left (or non-dominant) hand. The principal passive anterior drawer test involves taking the displacement reading on the dial indicator 220 at the approximately 20-pound force level indicated by the second audible beep. The readout on displacement dial indicator 220 will be directly in millimeters of anterior drawer displacement of tibial tubricle 50 relative to patella 52 and hence relative to the distal end of femur 42. If an anterior cruciate ligament compliance or end point test is to be conducted, then the number of millimeters of anterior drawer shift or excursion between the 15 and 20-pound force indicator beeps will be noted on the dial 220 for the 5-pound end point force differential. The ligament compliance in millimeters per pound will then be one-fifth of the drawer shift noted on the dial 220 between the 15 and 20-pound beeps.

If a posterior drawer test is to be performed with the knee testing device 160 so as to test the laxity of the posterior cruciate ligament, then the handle 244 will be pushed downwardly or posteriorly so as to displace the proximal end of tibia 40 downwardly or posteriorly relative to the patella 52 and hence the distal end of femur 42. The zeroing of displacement dial indicator 220 is accomplished in the same manner as for an anterior drawer test, and the same basic 20-pound drawer shift reading and 15 to 20-pound compliance or end point reading will be made as for the anterior drawer tests. However, the posterior drawer tests are preferably performed at a knee flexion angle of approximately 70°, and within a preferred knee flexion angle range of from about 70° to about 90°, instead of at the smaller flexion angle illustrated in FIG. 14.

The first and second transducer beeps indicate respective forces of 15 and 20 pounds applied to the handle 244. However, it is to be noted that the corresponding actual displacement forces applied at the knee joint 219 will be somewhat less because the force-applying lever arm between handle 244 and the fulcrum of distal tibial reference pad 178 is shorter than the distance between joint line 219 and reference pad 178.

It will be understood from the foregoing detailed description of the more complex and sophisticated embodiment 160 of the invention shown in FIGS. 7 to 15 that its principal advantage over the more simplified forms of the invention shown in FIGS. 1 to 6 is that it assures that all drawer shift readings are objective and at the same predetermined force levels, rather than being subjective and up to the feel and experience of the tester. This enables a more reliable determination of knee ligament condition to be made by comparison with statistical information formulated from tests made using the same objective force levels.

Applicant has developed extensive statistical information by utilizing the knee testing device 160 of FIGS. 7 to 15 in conducting tests on 828 knees. By comparing the results of knee tests made with any of the four forms of the invention specifically disclosed herein with such statistical information, the condition of an anterior or posterior cruciate ligament can be reliably determined.

The applicant's statistics show that two non-injured knees of the same patient will normally be substantially symmetrical for any particular anterior or posterior drawer test. This fact provides the basis for most knee testing in which any of the four disclosed forms of the invention are utilized. Thus, whenever either an anterior or a posterior ligament tear is suspected in an injured knee, identical comparative drawer tests are performed with the invention upon both the injured knee and the non-injured knee. Using such knee symmetry as a basis in extensive passive anterior drawer tests applied to a group of known chronic and acute anterior cruciate ligament deficit patients and to a normal population group, and the tests on the two groups are statistically quite distinct. Ninety-three percent of the known anterior cruciate ligament deficit patients had a difference of 3 millimeters or greater of anterior drawer shift between the injured and normal knees when an equal 20 pounds of anterior force was applied to both knees. On the other hand, 95 percent of the normals had a difference of 3 millimeters or less between both knees when the same test was applied. Although there was a small "gray zone" of injured and normal knee test overlap in the range of from 1 millimeter deviation to about 3.5 millimeters deviation between knees, these tests nevertheless have proven that if there is greater than 3 millimeters difference of anterior drawer shift with a 20-pound anterior force applied between the injured and non-injured knees of a patient, there is a very high probability that the injured knee involves a torn anterior cruciate ligament. Since these same tests showed that none of the normals had greater than 4 millimeters anterior drawer shift difference, the tests show that a torn anterior cruciate ligament is a substantial certainty if the anterior drawer shift difference is greater than 4 millimeters between the two knees of a patient upon application of the 20-pound anterior test force.

Figure 18:
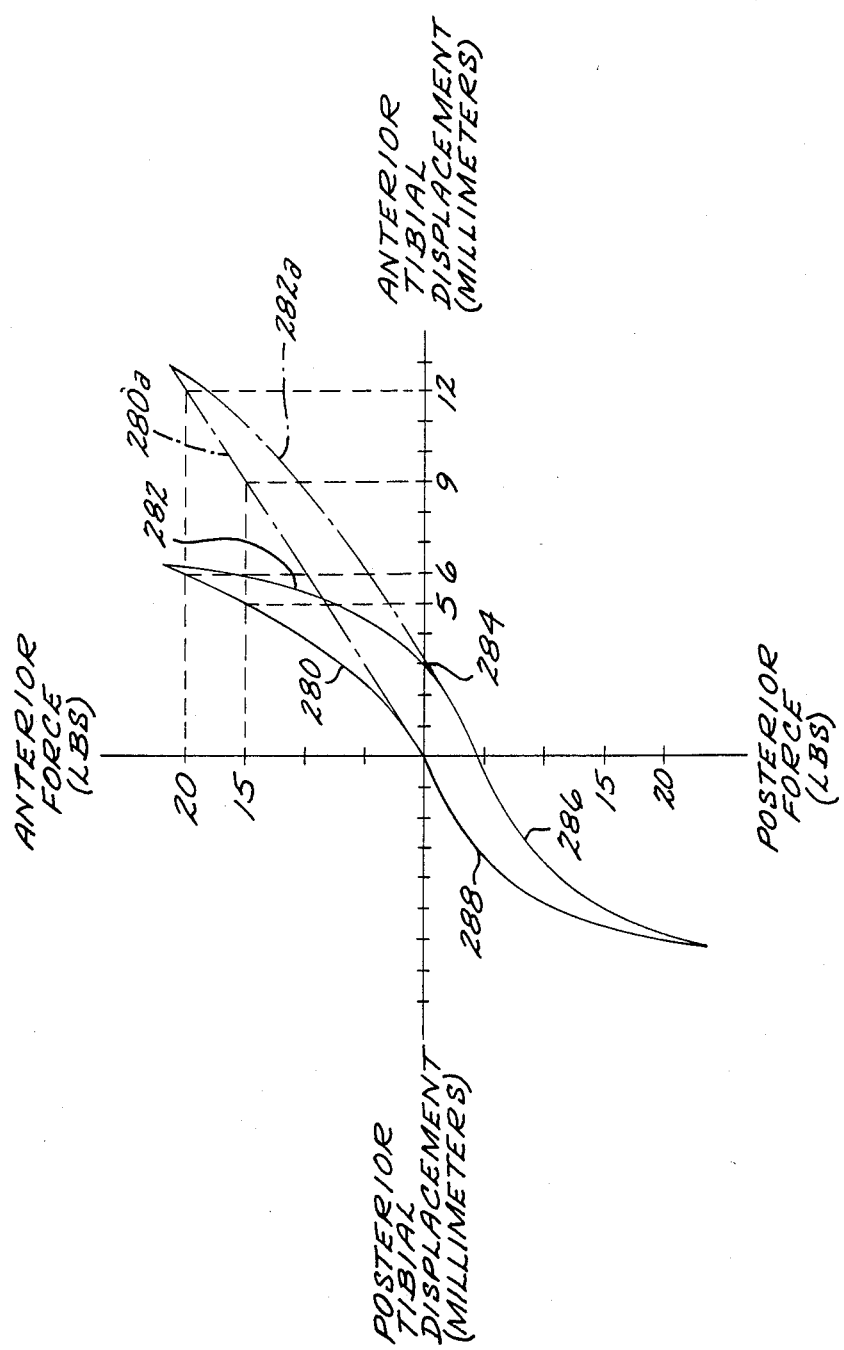
FIG. 18 is a graph illustrating the passive anterior drawer test and compliance or end point test differences between an average normal knee and an average knee with a torn anterior cruciate ligament.

FIG. 18 graphically illustrates the passive anterior drawer test and compliance or end point test differences between an average normal knee and an average knee with a torn anterior cruciate ligament. In the graph of FIG. 18, the ordinates represent pounds of anterior or posterior force and the abscissas represent resulting anterior or posterior drawer shift. The curves in FIG. 18 are based upon the aforesaid extensive statistical data derived by applicant utilizing the knee testing device 160 of FIGS. 7 to 15. Starting at the zero force and zero displacement point, the upwardly extending solid line curve portion 180 represents anterior tibial displacement resulting from anterior-directed force for an average normal knee. It will be seen from curve portion 280 that the average normal knee anterior displacement for 20 pounds of force is approximately 6 millimeters, and the average normal knee end point displacement between 15 and 20 pounds is approximately 1 millimeter. Again, starting at the zero force and zero displacement point, the upwardly extending phantom line curve portion 280a represents anterior tibial displacement resulting from anterior-directed force for an average knee with a torn anterior cruciate ligament. From curve portion 280a it will be seen that the average anterior displacement at 20 pounds of force for a knee having a torn anterior cruciate ligament is approximately 12 millimeters, with an end point displacement between 15 and 20 pounds of approximately 3 millimeters.

While these average differences between normal knees and knees with torn anterior cruciate ligaments are great, there is nevertheless such a wide variation in the 20 pound anterior drawer displacement for normal knees (all of the way from about 2 millimeters to about 12 millimeters) that the most reliable test results are achieved with the present invention by utilizing the aforesaid symmetry testing in which the injured and uninjured knees of the same person are compared.

Still referring to FIG. 18, the solid line curve section 282 and the phantom line curve section 282a represent the reduction of tibia-femur displacement that occurs upon removal of the anterior force in the respective average normal knee and average knee with a torn anterior cruciate ligament. It will be seen that when the force level is back down to zero, there will still be approximately 3 millimeters of anterior tibial displacement for each of the average normal and injured knees. This point on both curves is designated 284. Starting at the point 284, a posterior force on either the average normal knee or the average knee with a torn anterior cruciate ligament produces essentially the same force-displacement curve section 286; and removal of the posterior force results in essentially the same force-displacement curve section 288 for both the average normal knee and the average knee with a torn anterior cruciate ligament. Curve section 288 shows that upon complete removal of the posterior force, the tibia and femur return to their original zero displacement condition.

The wide disparity between the anterior force-displacement curve sections for the average normal knee and for the average knee with an anterior cruciate ligament tear illustrates the high degree of reliability that the present invention can achieve in the diagnosis of torn anterior cruciate ligaments, since the present invention has been proven in accurately measured cadaver tests to have a uniform accuracy to within less than 1 millimeter of displacement. There is a similar wide disparity in the force-displacement difference between the average normal knee and the average knee with a torn posterior cruciate ligament, although this difference has not been illustrated in FIG. 18. The fact that the posterior force-displacement curve sections 286 and 288 in FIG. 18 are essentially the same for the average normal knee and for the average knee with an anterior cruciate ligament tear illustrates that a posterior force-displacement test with the present invention to determine whether or not there is a posterior cruciate ligament tear is not adversely affected by the presence of a torn anterior cruciate ligament in the knee. Similarly, a torn posterior cruciate ligament in the knee does not adversely affect a test by the present invention to determine whether or not there is a torn anterior cruciate ligament.

The present invention has been shown in FIGS. 2, 3, 6 and 14, and described hereinabove in detail, as the several forms of the invention are employed in conducting passive anterior drawer tests. This is because the passive anterior drawer test is the most important of the tests that can be performed with the invention inasmuch as from 90 to 95 percent of all knee ligament tears are of the anterior cruciate ligament, and the passive anterior drawer test is the most sensitive test for determining whether or not there is an anterior cruciate ligament tear. Only 5 to 10 percent, and probably closer to 5 percent, of the knee ligament tears are of the posterior cruciate ligament.

The preferred knee flexion range of from about 20° to about 30° (with a preferred flexion of about 25°) for performing the passive anterior drawer test with the present invention has been established by the applicant because within this range the other knee stabilizers are the loosest and offer the least resistance to anterior movement of the tibia relative to the femur. Such other knee stabilizers include the medial and lateral collateral ligaments (respectively on the inside and outside of the leg), and the knee joint capsule which wraps around the knee joint from one side of the patella to the other.

The preferred knee flexion range of from about 70° to about 90° (with a prefered flexion of about 70°) for performing the passive posterior drawer test with the present invention has similarly been established by the applicant because within this range the knee capsule and collateral ligaments offer a minimum of resistance against posterior movement of the tibia relative to the femur. The 90° flexion angle is illustrated in FIGS. 16 and 21 for normal knee geometry. As is apparent from FIG. 21, in the 90° flexion position, the patella is accessible to engagement by the patellar reference pad of any of the disclosed forms of the invention.

To perform a passive posterior drawer test with any of the disclosed forms of the invention, the knee testing device is applied to the leg in the same manner as for a passive anterior drawer test, i.e. as illustrated in FIGS. 2, 3, 6 or 14, only with the knee flexion angle within the preferred range of from about 70° to about 90°, and a posterior force is applied to a proximal region of the tibia. For the first form of the invention shown in FIGS. 1 and 2, the posterior force will be applied to the upper surface 16 of reference arm 12 above proximal tibial reference pad 22. For the second form of the invention shown in FIG. 3, the posterior force will be applied to the top of the displacement indicator rod 26a, which may have a force-applying handle like the handle 36 of the first form for this purpose. With the third form of the invention, as illustrated in FIG. 6, the posterior force is applied against the top wall 88 of main case 82 directly above the reference pad 110. With the fourth form of the invention, as illustrated in FIG. 14, the posterior force is applied to the handle 244.

The passive posterior drawer test does not require the use of the thigh support platform 58 or foot support platform 60. The person being tested lies in a supine position with the knee up so as to have the desired flexion of about 70° to about 90°. The femur itself restrains the patella against posterior movement, so no separate stabilization counterforce is required as in the passive anterior drawer test.

As with the passive anterior drawer test, the passive posterior drawer test also preferably involves a comparison of the posterior drawer test for the injured knee with a posterior drawer test of the uninjured knee of the patient.

The passive anterior and posterior drawer tests are termed "passive" because they are performed with the leg muscles relaxed and quiet, i.e., passive. If either the quadriceps or the hamstrings are constricted during either the anterior or the posterior passive drawer test, it will interfere with the test results. Such muscular constriction or resistance as a result of patient guarding is much less of a problem with the present invention than with prior art apparatus and methods for testing cruciate ligaments because of the relative comfort of the invention when it is applied, the relatively small size of the invention, the minimal amount of manual manipulation of the patient that is required in performing a test, and the comfortable position of the patient during the test.

FIGS. 19 and 20 illustrate the active anterior drawer test, and FIGS. 21 and 22 illustrate the active posterior drawer test. These active drawer tests are a different catergory of tests from the passive anterior and posterior drawer tests heretofore described. In the performance of the active drawer tests, the displacement force that is employed is applied by contraction of the quadriceps, as distinguished from the hand-applied forces employed in the passive drawer tests heretofore described.

The major active drawer test is the active anterior drawer test illustrated in FIGS. 19 and 20, since it is the anterior cruciate ligament that is most likely to get torn. While any of the four forms of the invention described above may be employed in the active drawer tests, the preferred form for accomplishing these tests is the knee testing device 160 shown in FIGS. 7–15. The testing device is applied to the tibia 40 and patella 52 in the same manner as shown in FIG. 14 and as described in detail hereinabove, but the testing device 160 has not been shown in the active drawer diagrams of FIGS. 19–22 in order to simplify the illustrations.

For the active anterior drawer test illustrated in FIGS. 19 and 20, the leg is supported as shown in FIG. 14 at a flexion angle in the range of from about 20° to about 30°, and preferably approximately 25°. Referring to FIG. 14 along with FIGS. 19 and 20, the patellar reference pad 202 is stabilized on the patella 52 by a steady posterior pressure on counterforce application pad 214, and then the knee is set in the reference position by a brief posterior push on force-applying handle 244 which, as seen in FIG. 19, will displace the proximal end of tibia 40 posteriorly relative to the distal end of femur 42, the amount of displacement depending upon the injured or non-injured condition of the anterior cruciate ligament. Preferably, this posterior force on handle 244 will be the same for each active anterior drawer test so as to standardize the tests, and to provide an accurate comparison between the normal and injured knees of a particular patient; a suitable posterior force on handle 244 for this purpose being approximately 15 pounds as indicated by the first beep. In this displaced condition of the knee joint, the displacement dial indicator 220 is rotated to the zero position. Then, while keeping the steady posterior pressure on the patellar reference pad 202, the active drawer test is performed by asking the patient to gently raise his heel off of the table or foot support platform 60. This will cause the patient to contract the quadriceps 54, which will apply a force through the patellar tendon 56 to the tibial tubricle 50 along a force line 290 that is anteriorly angularly offset relative to the joint compression force line 292 by an angle designated 294. Thus, it will be seen that there is an anterior force component of the patellar tendon line of force 290 relative to the joint compression force line 292 which will shift the tibia 40 anteriorly relative to the femur 42 from the displaced position of FIG. 19 to the normal position of FIG. 20 where it is stopped by the posterior cruciate ligament. The amount of drawer shift between the positions of FIGS. 19 and 20 will be indicated directly in millimeters on the displacement dial indicator 220.

Completion of the drawer shift from the position of FIG. 19 to the position of FIG. 20 is indicated by the fact that the displacement dial indicator 220 shows a maximum displacement and moves no further; or by a reversal of the direction of the dial indicator 220 which may be caused as the heel starts to lift, such reversal being caused by anterior movement of the fulcrum or distal end of the testing device 160.

The extensive testing that has been performed by the applicant indicates that this active anterior drawer test in the normal population averages about 70 percent of the magnitude of the passive anterior drawer test previously described, and that this relationship remains relatively constant over the range of patients with tight (approximately 2 mm) normal knees up to patients with loose (approximately 11 mm) normal knees. As with the passive anterior drawer test, the determination by means of the active anterior drawer test as to whether or not the patient has a torn anterior cruciate ligament is made by comparing active anterior drawer tests on the injured and uninjured knees of the patient.

The active drawer test for the posterior cruciate ligament is illustrated in FIGS. 21 and 22, and although any of the four knee testing devices described hereinabove may be used for this test, it is preferred to employ the knee testing device 160 of FIGS. 7–15. For this test, the patient lies in a supine position with both knees up to a flexion angle in the range of from about 70° to about 90°. Within this range there will be a neutral flexion angle, which is illustrated in FIG. 21, at which the uninjured reference or control knee has its patellar tendon force line 290a exactly parallel to its joint compression force line 292a, so that contraction of the quadriceps will cause no anterior or posterior shift of the tibia 40 relative to the femur 42 since there is no anterior or posterior force component. This specific neutral flexion angle for the uninjured knee may be determined by making a first active posterior drawer test thereon, and if the flexion angle is too great, there will be a small posterior component of the posterior tendon force line 290a relative to the joint compression force line 292a which will cause a slight posterior tibial displacement during the active drawer test. If such is the case, then the flexion angle is decreased and further active posterior drawer tests made as required until there is no substantial posterior or anterior force component of the patellar tendon force line 290a relative to the joint compression force line 292a, and consequently no tibial displacement during the active posterior drawer test. Typically, in a normal knee near 90° of flexion, there will be a small posterior component to the patellar tendon force line 290a relative to the joint compression force line 292a, and also typically, the neutral angle of flexion will be around 75° of flexion, although this will, of course, vary for different patients. If, during the initial active posterior drawer test on the uninjured knee results in anterior tibial displacement caused by an anterior force component of the patellar tendon force line 290a relative to the joint compression force line 292a, then the flexion angle of the knee joint should be increased as required to achieve the specific neutral flexion angle for that particular patient's uninjured knee.

To make the active posterior drawer test, the knee testing device 160 is attached to the tibia generally as shown in FIG. 14, but with the knee flexed generally as shown in FIG. 21, being sure that the patellar reference pad 202 rests only upon the patella 52 totally proximal to the patellar tendon 56 and not in contact with the patellar tendon 56, as such contact with the patellar tendon 56 would introduce a measurement error when it is tensioned. To conduct the test, the examiner sits on the patient's foot and asks the patient to try to gently slide the foot forward. The resulting contraction of the quadriceps muscles 54 applies the desired tensioning force to the patellar tendon 56 for the test. When the particular neutral flexion angle has thus been established for the patient, the injured knee is arranged at this same particular flexion angle and the testing device 160 is attached to the tibia 40 in the same manner as it had been attached to the tibia 40 of the uninjured leg. A posterior push on the handle 244 of the device 160 will cause a posterior sag of the tibia 40 relative to the femur 42 as shown in FIG. 22; or if there is substantial knee joint capsule damage, the force of gravity, as indicated by arrow 296, will cause such posterior tibial sag. Preferably, the active posterior drawer tests are standarized with a posterior push on handle 244 of 15 pounds, as indicated by the first beep, to set the knee joint in preparation for the test.

The adjustment slide 206 and displacement dial indicator 220 are then adjusted as required to place the dial indicator 220 in its zeroed position, and with the examiner sitting on the foot of the injured leg, the patient is asked to try to gently slide the foot forward. As seen in FIG. 22, with the tibia 40 substantially posteriorly displaced relative to the femur 42 due to the laxity of a torn posterior cruciate ligament, the patellar tendon force line 290a will be directed at a substantial anterior angle 294a relative to the joint compression force line 292a, the resulting anterior force component on tibia 40 upon contraction of the quadriceps muscles 54 causing the tibia 40 to spring anteriorly relative to the femur 42 to the neutral position illustrated in FIG. 21 in which the force lines 290a and 292a are substantially parallel. The amount of the drawer shift will then be directly readable in millimeters on the displacement dial indicator 220.

Figure 23:
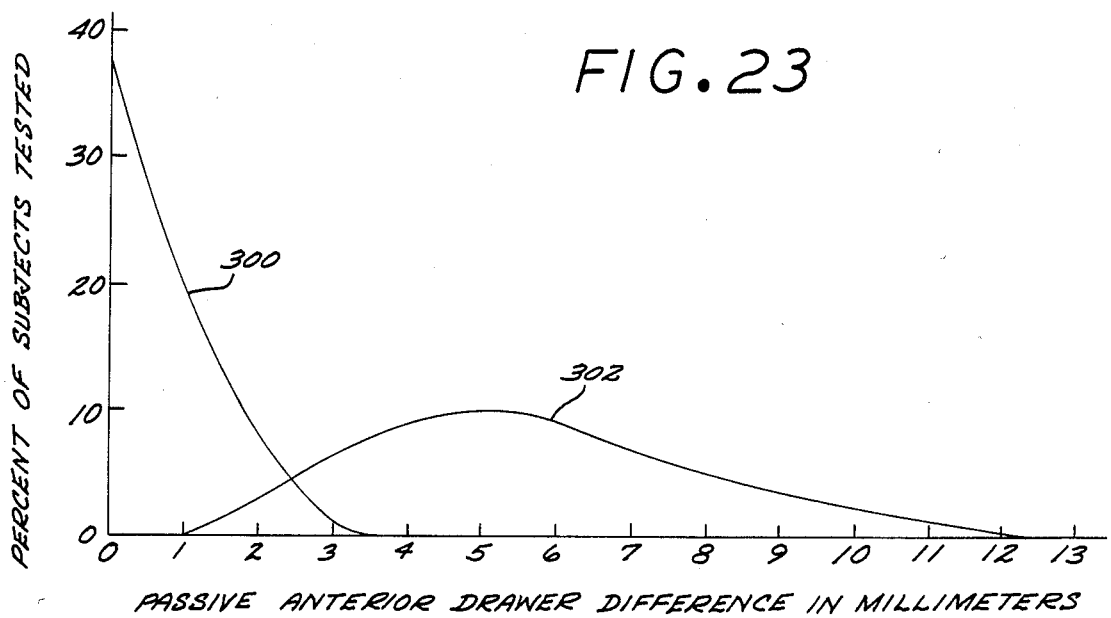
FIG. 23 graphically illustrates statistical information for the passive anterior drawer difference between normal knees and known anterior cruciate deficit knees.
Figure 24:
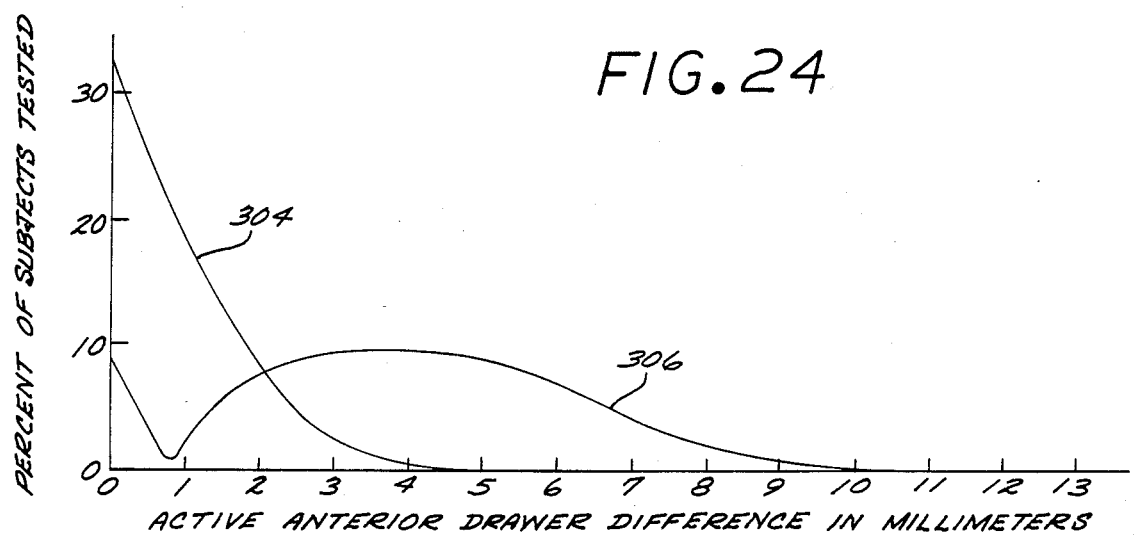
FIG. 24 is a view similar to FIG. 23, but illustrating the active anterior drawer difference between normal knees and knees having a known anterior cruciate ligament deficit.
Figure 25:
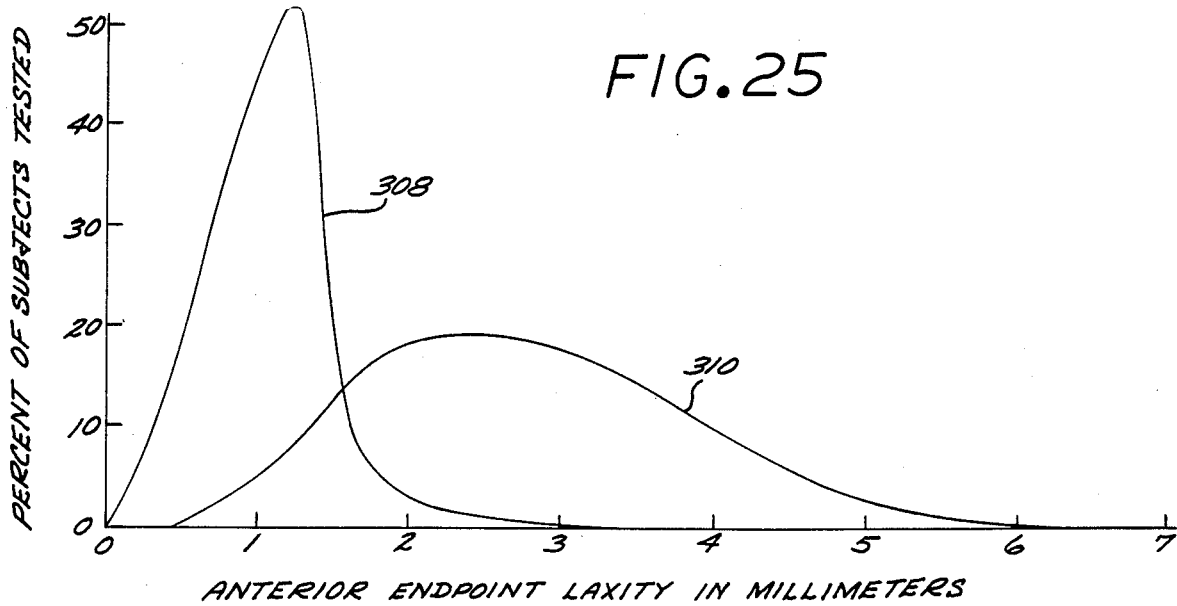
FIG. 25 is a view similar to FIGS. 23 and 24 but illustrating the anterior end point laxity between 15 and 20 pounds of anterior force for normal knees and for knees having a known anterior cruciate ligament deficit.

FIGS. 23, 24 and 25 graphically illustrate some of the statistical information which the applicant has developed utilizing the knee testing device 160 of FIGS. 7-15 in comparative tests between normal knees and knees having known chronic anterior cruciate ligament deficits.

FIG. 23 graphically illustrates the passive anterior drawer test in the range of from about 20° to about 30° of knee flexion. The abscissas represent the drawer shift difference in millimeters between the uninjured and injured knees of the subjects tested, while the ordinates represent the percent of subjects tested. Curve 300 was developed from 414 normal population subjects (i.e., subjects having normal anterior cruciate ligaments), while curve 302 was developed from 118 subjects having known chronic anterior cruciate ligament deficit knees. Curve 300 for the normal population shows that approximately 95 percent of the normals had a difference of 3 mm or less, and approximately 90 percent of the normals had a difference of only about 1 mm or less between both knees for the 20-pound anterior drawer test. On the other hand, the curve 302 shows that approximately 93 percent of the known chronic anterior cruciate ligament deficit patients had a difference of 3 mm or greater, and none had a difference less than 1 mm, of anterior drawer shift between the injured and normal knees for the 20-pound anterior drawer test. Despite the small overlapping zone between the curves 300 and 302 between about 1 and about 3.5 mm deviation between knees, these curves illustrate the very high probability with which a torn anterior cruciate ligament can be determined with the present invention.

FIG. 24 illustrates the active anterior drawer test in the range of from about 20° to about 30° of knee flexion. The abscissas represent the drawer shift difference in millimeters between the uninjured and injured knees resulting from quadriceps contraction of the subjects tested, while the ordinates represent the percent of subjects tested. Curve 304 was developed from 408 normal population subjects, and curve 306 was developed from 118 subjects having known chronic anterior cruciate deficit knees. The somewhat larger amount of overlap between the active anterior drawer difference curves 304 and 306 of FIG. 24 than the overlap between the passive anterior drawer difference curves 300 and 302 of FIG. 23 illustrates the fact that the active anterior drawer test is not quite as sensitive as the passive anterior drawer test. However, in the case of a recent, acute injury (being tested within approximately 7 days of the injury), when the knee is usually still swollen and painful, the patient tends to be more relaxed during an active anterior drawer test than during a passive anterior drawer test, so that under this circumstance, the active anterior drawer test is generally more useful than the passive anterior drawer test.

FIG. 25 graphically illustrates the compliance or end point test, which is the most useful test for determining whether or not there is a torn ligament in a knee with an acute injury. The anterior end point test illustrated in FIG. 25 is also performed in the range of from about 20° to about 30° of knee flexion. The abscissas represent the amount of anterior drawer shift in millimeters between 15 and 20 pounds of pull on the handle 244 of testing device 160, while the ordinates again represent the percent of subjects tested. Curve 308 was developed from 408 normal population subjects, while curve 310 was developed from 118 subjects having known chronic anterior cruciate deficit knees. It will be seen from curve 308 that the average normal knee has an anterior cruciate ligament laxity between the 15 and 20 pound points of approximately 1 mm, while the average known anterior cruciate deficit knee has an anterior cruciate laxity between the 15 and 20 pound points of approximately 2.5 mm. It is also notable that this average end point laxity of approximately 1 mm for the normal knee population represented by curve 308 was between an average of approximately 5 mm to approximately 6 mm of total anterior drawer shift between the 15 and 20 pound points, while the approximately 2.5 mm laxity average for the known deficit knees represented by curve 310 was between approximately 9.5 and approximately 12 mm of total anterior drawer shift between the 15 and 20 pound points.

The tests previously described herein include passive anterior and posterior drawer tests wherein the patient's muscles are relaxed, active anterior and posterior drawer tests utilizing voluntary contraction of the patient's quadriceps, and ligament end point or compliance tests which are also either anterior or posterior tests. An additional test not previously mentioned which may be usefully performed with the present invention is the maximal drawer test, which is a high force drawer shift measurement for either the anterior or the posterior cruciate ligament.

While the preferred flexion angles and angle ranges have been described herein for the various tests, it is to be understood that the present invention may be employed in any of the tests with the knee set at any desired flexion angle that may be considered useful by the person performing the tests.

The present invention is not only useful to determine whether or not a patient has suffered a torn cruciate ligament, but is also useful during the course of knee reconstruction, starting in the operating room. Thus, the apparatus of the present invention, preferably in the form shown in FIGS. 7–15, may be enclosed in a sterile bag, and the surgeon can check his cruciate ligament repair or reconstruction work during surgery, checking to see that the repaired ligament is neither too tight nor too loose, and correcting it during surgery. Then, during rehabilitation of the patient after surgery, the invention may be usefully employed to verify the knee stability that has been achieved by the surgery.

While the instant invention has been shown and described here in what are conceived to be the most practical and preferred embodiments, it is recognized that departures may be made therefrom within the scope of the invention, which is therefore not to be limited to the details disclosed herein, but is to be accorded the full scope of the appended claims.

We claim:

1. A method of testing a cruciate knee ligament which comprises the steps of:
   making a determination of first locations relative to each other, in the general anterior/posterior direction, of the tibial tubrical and patellar bone structures adjacent the knee joint of a leg by engaging first and second locating members directly against the anterior surface of the leg in registry with the tibial tubrical and patellar bone structures, respectively, and making a first comparison of the relative positions of said locating members in the general anterior/posterior direction;
   while maintaining said engagement of said locating members against said leg, applying a force to the proximal tibia of said leg in the general anterior/posterior direction, with said patellar bone structure being restrained against movement, so as to relatively displace said bone structures from their said first relative locations to second locations relative to each other in the general anterior/posterior direction which will cause a corresponding relative displacement between said locating members; and
   while said force is being applied making a determination of said second relative locations of said bone structures by making a second comparison of the relative positions of said locating members in the general anterior/posterior direction;
   the difference between said second and first comparisons of the relative positions of said locating members indicating the amount of tibia/femur drawer shift at said knee joint.

2. The method of claim 1, which comprises:
   performing said method steps relative to an injured knee joint of a person;
   performing said method steps relative to an uninjured knee joint of said person; and
   comparing the amount of said drawer shift of said injured knee joint with that of said uninjured knee joint.

3. The method of claim 1, wherein said force is directed generally anteriorly for testing the anterior cruciate ligament of said knee joint.

4. The method of claim 3, wherein said patellar bone structure is restrained against anterior movement by applying a posterior stabilization counterforce to said patellar bone structure.

5. The method of claim 3, wherein said leg is arranged with said knee joint at a flexion angle within the range of from approximately 20° to approximately 30°.

6. The method of claim 5, wherein said knee joint is supported within said flexion angle range by means of a posterior thigh support platform.

7. The method of claim 6, wherein the rotational angle of the tibia of said leg is maintained substantially constant by means of a foot support platform which supports the foot of said leg against external rotation.

8. The method of claim 3, wherein said force is applied against the calf of said leg so as to perform a passive anterior drawer test.

9. The method of claim 3, wherein said force is applied by contraction of the quadriceps muscles of said leg to perform an active anterior drawer test.

10. The method of claim 1, wherein said force is directed generally posteriorly for testing the posterior cruciate ligament of said leg.

11. The method of claim 10, wherein said patellar bone structure is restrained against posterior movement by the femur of said leg.

12. The method of claim 10, wherein said leg is arranged with said knee joint at a flexion angle within the range of from approximately 70° to approximately 90°.

13. The method of claim 10, wherein said force is applied against said tibial tubricle bone structure so as to perform a passive posterior drawer test.

14. The method of claim 1, wherein said tibial tubricle bone structure is initially displaced posteriorly relative to said patellar bone structure, and said force is directed generally anteriorly and applied by contraction of the quadriceps muscles of said leg to perform an active posterior drawer test.

15. The method of claim 1, wherein said force is applied at a predetermined, measured force level.

16. The method of claim 15, wherein said force level is approximately twenty pounds.

17. The method of claim 1, which comprises an "end point" test, wherein an initial force at a first predetermined force level is applied in the general anterior/posterior direction while determination of said first relative locations is made, and said force that is applied while making said determination of said second relative location is at a second predetermined force level that is higher than said first force level.

18. The method of claim 17, wherein said first force level is approximately fifteen pounds and said second force level is approximately twenty pounds.

* * * * *